United States Patent
Niibe et al.

(10) Patent No.: US 11,661,584 B2
(45) Date of Patent: May 30, 2023

(54) METHOD FOR MAINTAINING UNDIFFERENTIATION POTENCY OF MESENCHYMAL STEM CELL EMPLOYING SHAKING SUSPENSION CULTURE

(71) Applicant: TOHOKU UNIVERSITY, Miyagi (JP)

(72) Inventors: Kunimichi Niibe, Miyagi (JP); Hiroshi Egusa, Miyagi (JP)

(73) Assignee: TOHOKU UNIVERSITY, Miyagi (JP)

(*) Notice: Subject to any disclaimer, the term of this patent is extended or adjusted under 35 U.S.C. 154(b) by 664 days.

(21) Appl. No.: 16/606,081

(22) PCT Filed: Apr. 20, 2018

(86) PCT No.: PCT/JP2018/016321
§ 371 (c)(1),
(2) Date: Dec. 12, 2019

(87) PCT Pub. No.: WO2018/194161
PCT Pub. Date: Oct. 25, 2018

(65) Prior Publication Data
US 2021/0139855 A1 May 13, 2021

(30) Foreign Application Priority Data
Apr. 20, 2017 (JP) .............................. JP2017-083483

(51) Int. Cl.
*C12N 5/0775* (2010.01)
(52) U.S. Cl.
CPC ........ *C12N 5/0668* (2013.01); *C12N 2527/00* (2013.01)
(58) Field of Classification Search
None
See application file for complete search history.

(56) References Cited

FOREIGN PATENT DOCUMENTS

| JP | 2005-278910 | 10/2005 |
|---|---|---|
| JP | 2013-536696 | 9/2013 |
| WO | 2004/065586 | 8/2004 |
| WO | 2012/032521 | 3/2012 |

OTHER PUBLICATIONS

Siddiquee & Sha, "Microcarrier-Based Expansion of Adipose-Derived Mesenchymal Stem Cells in Shake Flasks" (Jan. 2014), vol. 12 (4): 32-38. (Year: 2014).*

International Search Report dated Jun. 26, 2018 in International (PCT) Application No. PCT/JP2018/016321.
Wen et al., "Serum-Free Spheroid Suspension Culture Maintains Mesenchymal Stem Cell Proliferation and Differentiation Potential", Biotechnol. Prog., vol. 30, No. 4, pp. 974-983.
Lin et al., "Expansion in microcarrier-spinner cultures improves the chondrogenic potential of human early mesenchymal stromal cells", Cytotherapy, vol. 18, 2016, pp. 740-753.
Shekaran et al., "Enhanced in vitro osteogenic differentiation of human fetal MSCs attached to 30 microcarriers versus harvested from 20 monolayers", BMC Biotechnology, vol. 15, No. 102, 2015, pp. 1-13.
Hatano et al., "A clinical long-term radiographic evaluation of graft height changes after maxillary sinus floor augmentation with a 2 : 1 autogenous bone/xenograft mixture and simultaneous placement of dental implants", Clin. Oral Impl. Res., vol. 15, 2004, pp. 339-345.
Verhoeven et al., "Onlay grafts in combination with endosseous implants in severe mandibular atrophy: one year results of a prospective, quantitative radiological study", Clin. Oral Impl. Res., vol. 11, 2000, pp. 583-594.
Pittenger et al., "Multilineage Potential of Adult Human Mesenchymal Stem Cells", Science, vol. 284, Apr. 2, 1999, pp. 143-147.
Morikawa et al., "Development of mesenchymal stem cells partially originate from the neural crest", Biochemical and Biophysical Research Communications, vol. 379, 2009, pp. 1114-1119.
Morikawa et al., "Prospective identification, isolation, and systemic transplantation of multipotent mesenchymal stem cells in murine bone marrow", J. Exp. Med., vol. 206, No. 11, 2009, pp. 2483-2496.
Houlihan et al., "Isolation of mouse mesenchymal stem cells on the basis of expression of Sca-1 and PDGFR-α", Nature Protocols, vol. 7, No. 12, 2012, pp. 2103-2111.
Mabuchi et al., "LNGFR$^+$THY-I$^+$VCAM-I$^{hi+}$ Cells Reveal Functionally Distinct Subpopulations in Mesenchymal Stem Cells", Stem Cell Reports, vol. 1, Aug. 6, 2013, pp. 152-165.
Bonab et al., "Aging of mesenchymal stem cell in vitro", BMC Cell Biology, vol. 7, No. 14, 2006, pp. 1-7.
Bork et al., "DNA methylation pattern changes upon long-term culture and aging of human mesenchymal stromal cells", Aging Cell, vol. 9, 2010, pp. 54-63.
Baraniak et al., "Scaffold-free culture of mesenchymal stem cell spheroids in suspension preserves multilineage potential", Cell Tissue Res., vol. 347, No. 3, Mar. 2012, pp. 701-711.
Doetsch et al., "Subventricular Zone Astrocytes Are Neural Stem Cells in the Adult Mammalian Brain", Cell, vol. 97, Jun. 11, 1999, pp. 703-716.
Pacey et al., "Neural Stem Cell Culture: Neurosphere generation, microscopical analysis and cryopreservation", https://protocolexchange.researchsquare.com/article/nprot-77/v1, Protoc Exch Doi: 10:1038/nprot.2006.215, 2006, pp. 1-15.

* cited by examiner

Primary Examiner — Teresa E Knight
(74) Attorney, Agent, or Firm — Wenderoth, Lind & Ponack, L.L.P.

(57) ABSTRACT

Provided is a method of culturing mesenchymal stem cells as a cell construct while maintaining undifferentiation thereof, the method including subjecting mesenchymal stem cells to shaking culture.

7 Claims, 17 Drawing Sheets
Specification includes a Sequence Listing.

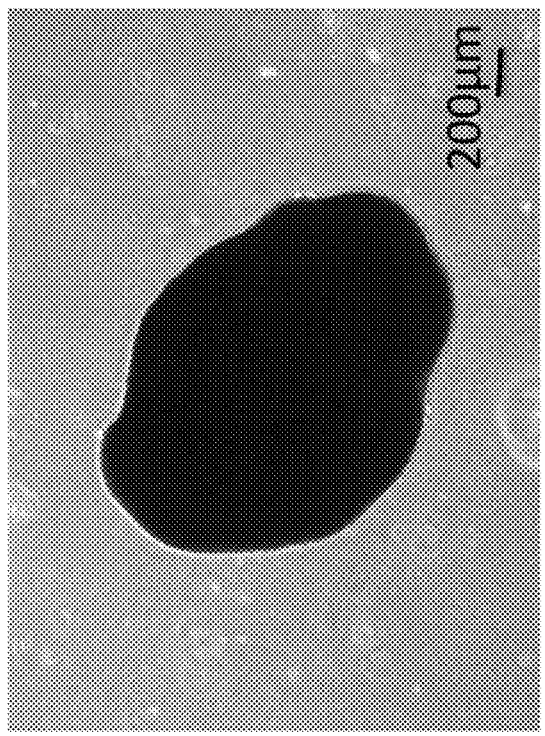
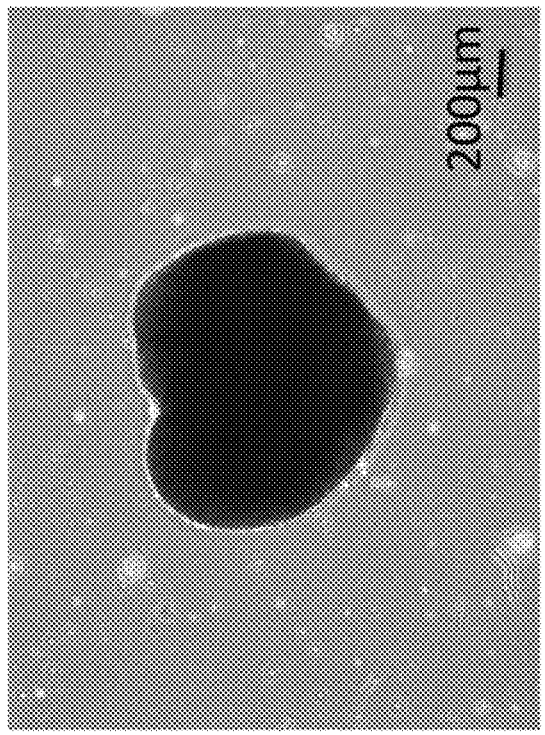
FIG. 1

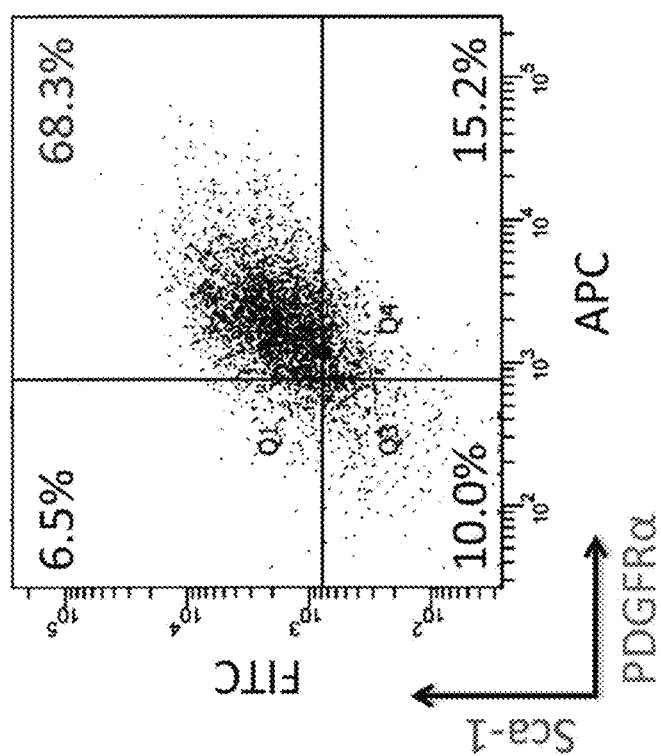
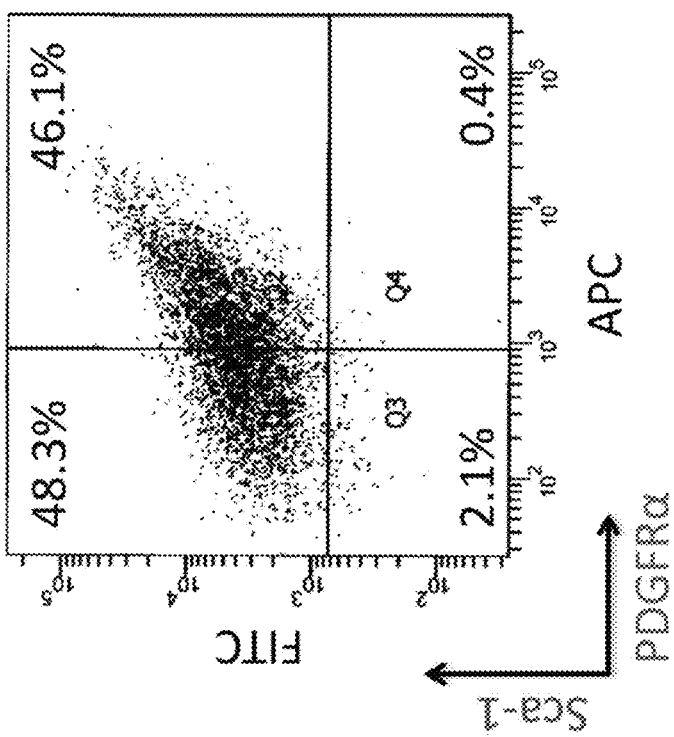
Fig.2b

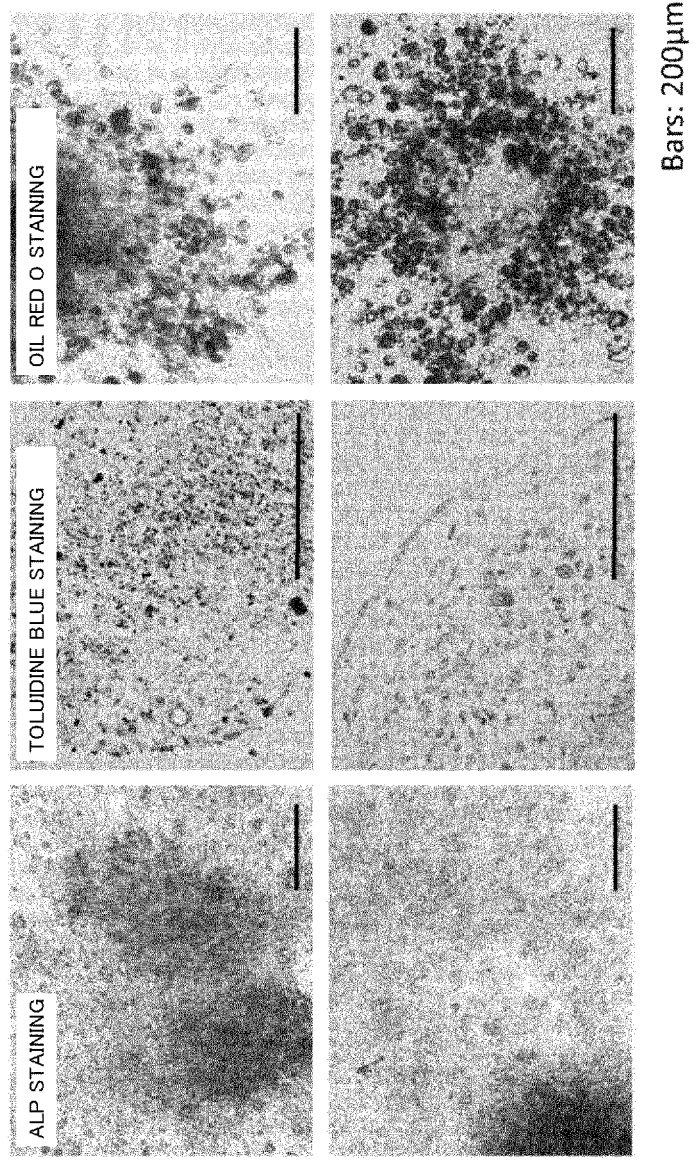

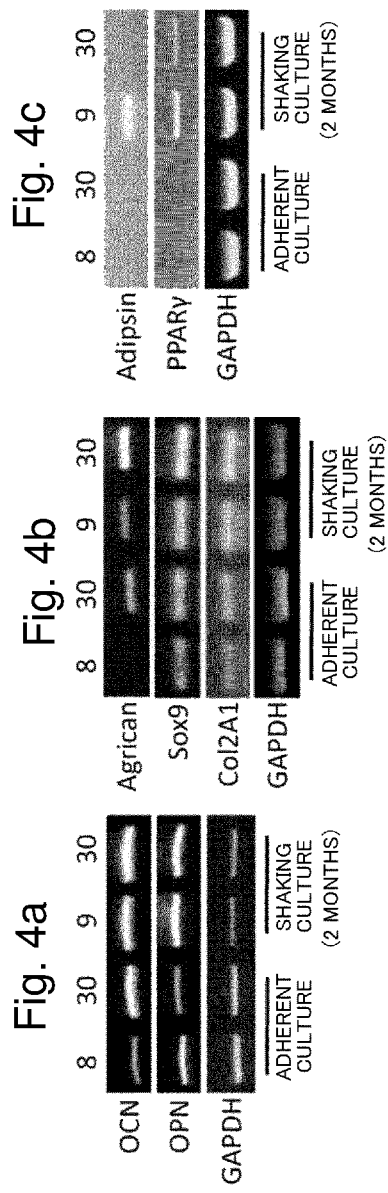

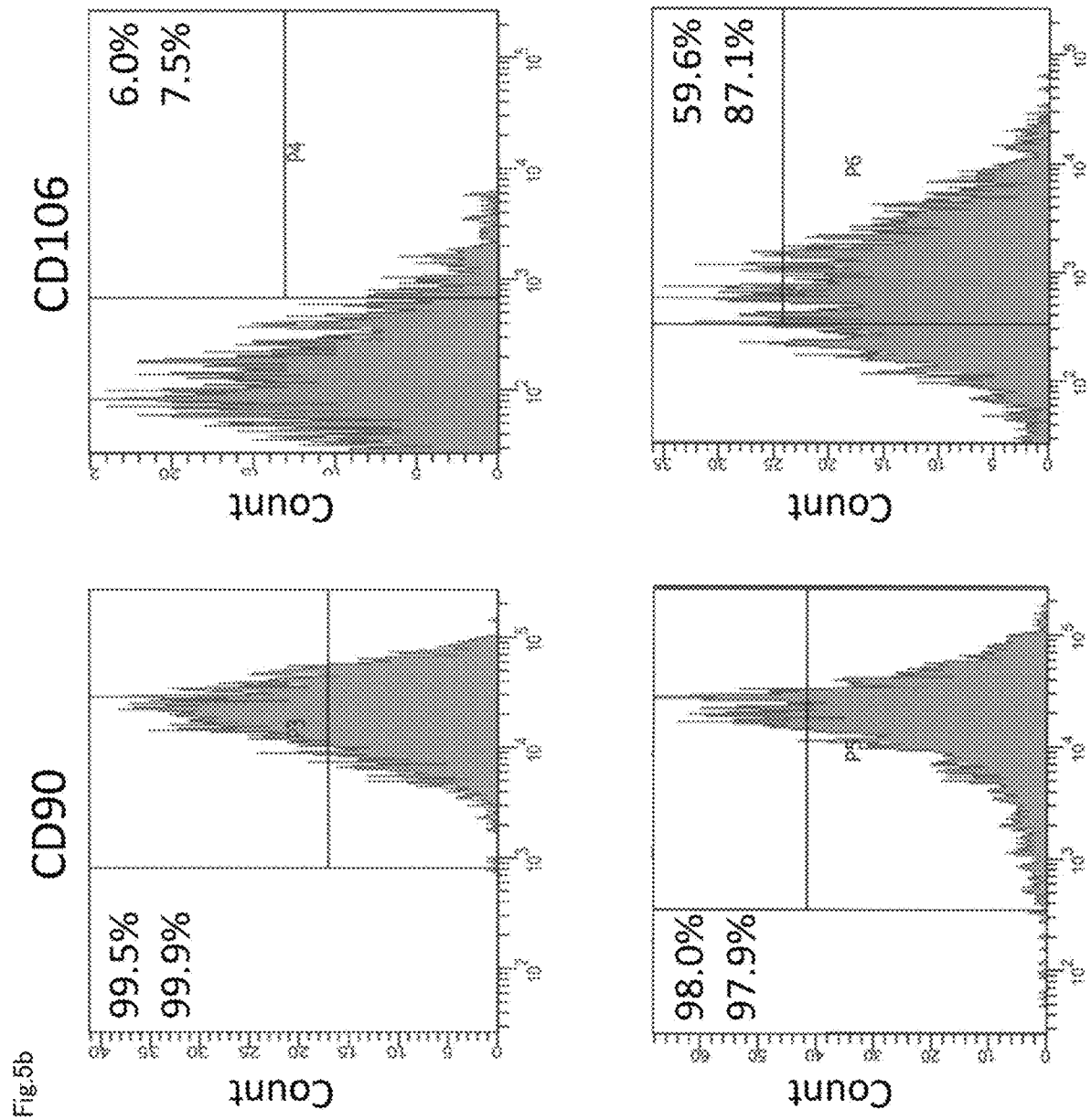

Fig. 6a
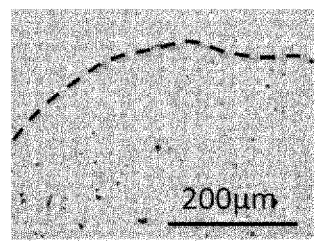
Fig. 6b
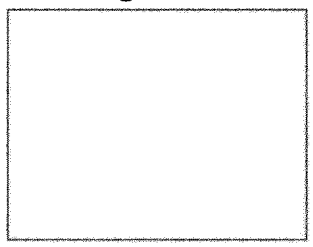
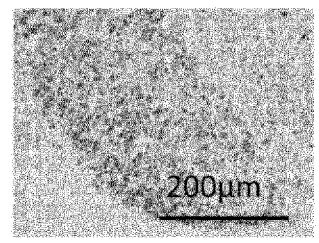
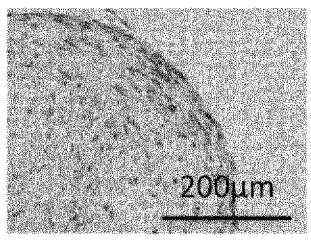

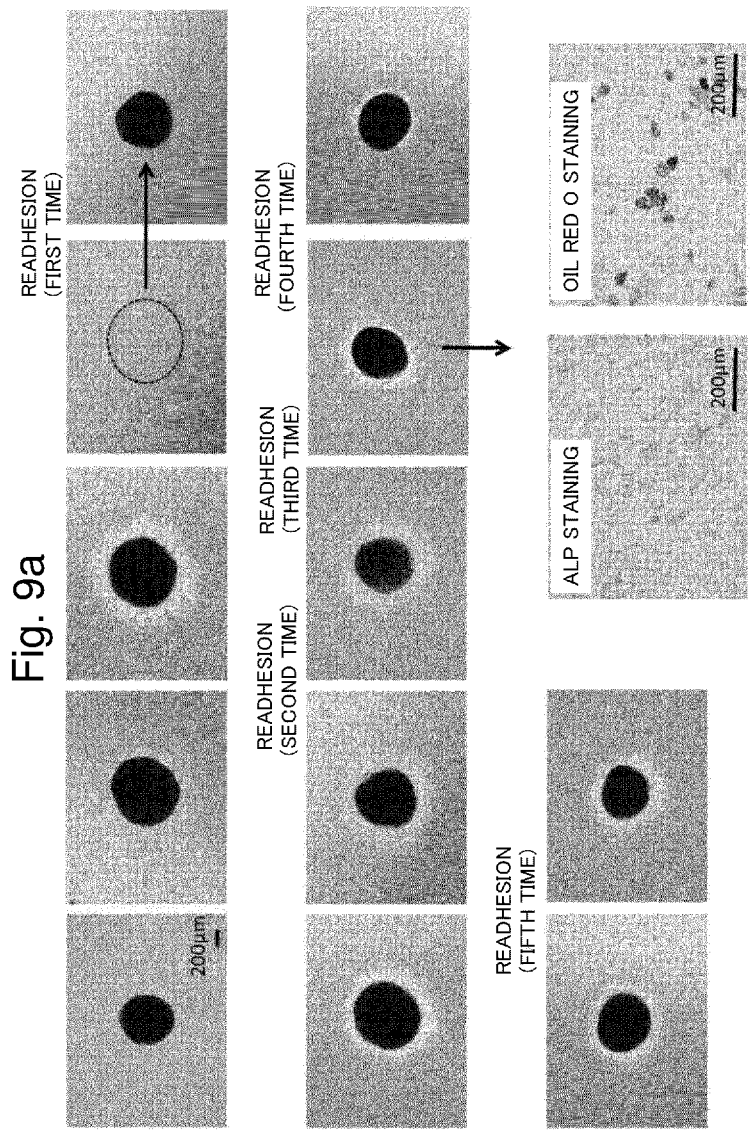

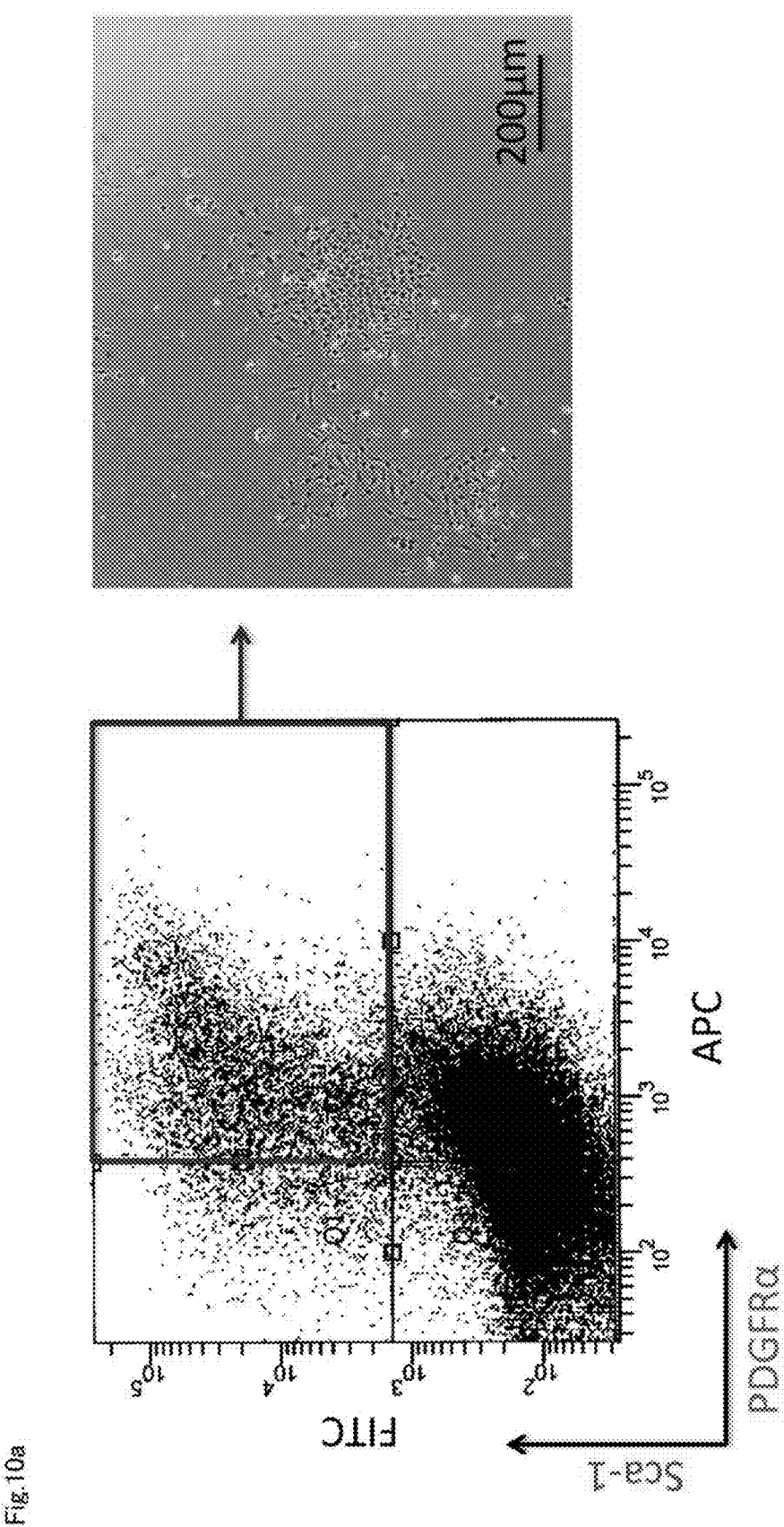

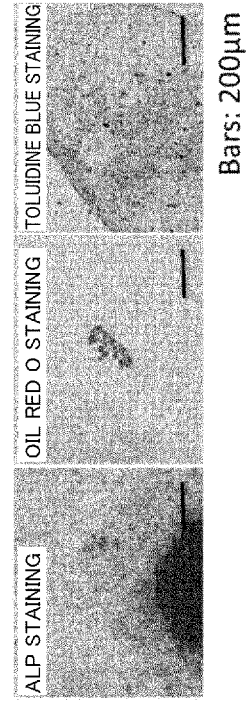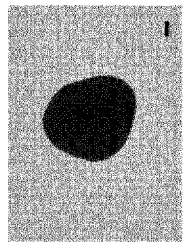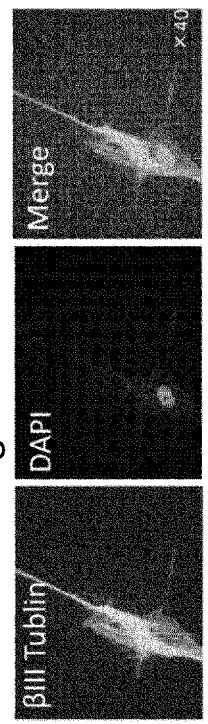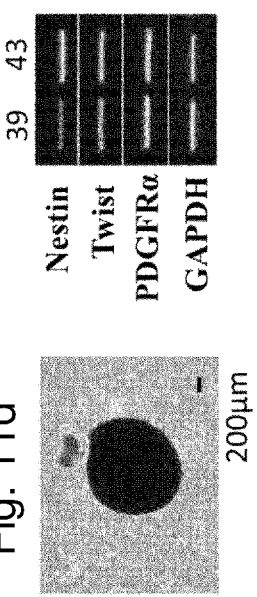

METHOD FOR MAINTAINING UNDIFFERENTIATION POTENCY OF MESENCHYMAL STEM CELL EMPLOYING SHAKING SUSPENSION CULTURE

TECHNICAL FIELD

The present invention relates to mesenchymal stem cells and a culture method therefor.

BACKGROUND ART

In the field of medicine and the field of dentistry, reconstruction/implant treatment with an artificial material made of β-TCP or the like or with titanium or autologous bone transplantation is performed for a substantial defect of a bone tissue. In treatment involving using an artificial material, including autologous bone transplantation, there is a problem of absorption of a regenerated bane occurring after the treatment (Non-patent Literatures 1 and 2). In addition, in the field of bone regeneration, a scaffold or a membrane for preventing infiltration of granulation tissue is often required for space making at the time of surgery, and an influence thereof in a regeneration site also needs to be taken into consideration.

In addition, in recent years, research and treatment involving vising autologous cells have also been performed, and mesenchymal stem cells (MSCs) typify such cells (hereinafter as well, the mesenchymal stem cells are abbreviated as MSCs).

The MSCs are cells originally defined as cells that adhere and grow when bone marrow cells are seeded in a plastic culture dish, and that have an ability to differentiate into mesodermal tissues and cells, such as fat, cartilage, and bone (Non-patent Literature 3).

Searches have been made for markers for mouse bone marrow MSCs, and it was reported in 2009 by Morikawa et al., who used a flow cytometer, that mouse MSCs were concentrated in a PI$^-$/CD45$^-$/Ter119$^-$/Sca-1$^+$/PDGFRα$^+$ fraction (Non-patent Literatures 4 and 5). Details of this purification technology have been disclosed by Houlihan et al. (Non-patent Literature 6). Human bane marrow MSCs have been reported by Mabuchi et al. to be contained in a CD271 (LNGFR)$^+$/CD90 (Thy-1)$^+$ fraction at a high concentration (Non-patent Literature 7).

The MSCs are present in various tissues, but in general, it is bone marrow that is a tissue from which many MSCs can be stably acquired. The MSCs are defined as cells that adhere and grow when cells in bone marrow are seeded in a plastic culture dish, and that are capable of differentiating into osteoblasts, chondrocytes, and adipocytes (Non-patent Literature 3), and have attracted attention as a cell supply source in regenerative medicine. However, when the MSCs are repeatedly subjected to adherent culture for a long period of time, their proliferative capacity and differentiation ability are reduced, leading to a clinical problem in that results differ between facilities or between patients.

Specifically, it is known that related-art MSCs have a limit on their proliferative capacity under an adherent culture environment, and also lose their differentiation ability accordingly (Non-patent Literatures 8 and 9). It is known that even purified MSCs undergo a gradual reduction in proliferative capacity under an adherent culture environment (see FIG. 1G of Non-patent Literature 5).

In recent years, it has been reported that, when the MSCs are cultured on a special culture dish, three-dimensional cell constructs (spheres or spheroids) of the MSCs can be formed in a suspension state without adhering to the culture dish (Non-patent Literature 10). However, long-term culture cannot be performed by this method, and there is no report on how the cells change when cultured in a suspension environment.

CITATION LIST

Non-Patent Literature

NPL 1: Hatano et al. Clin Oral Impl Res, vol. 15, p 339 to 345, 2004
NPL 2: Verhoeven et al. Clin Oral Impl Res, vol. 11, p 583 to 594, 2000
NPL 3: Pittenger et al. Science, vol 284 2 Apr. 1999
NPL 4: Morikawa et al. BBRC, vol. 379, p 1114 to 1119, 2009.
NPL 5: Morikawa et al. JEM, vol. 206, p 2483 to 2496, 2009.
NPL 6: Houlihan et al. Nature Protocol, vol. 7(12), p 2103 to 2111, 2012.
NPL 7: Mabuchi et al. Stan cell reports, vol. 1(2), p 152 to 165, 2013
NPL 8: Bonab et al. BMC Cell Biol, vol. 7, p 14, 2006.
NPL 9: Bork et al. Aging Cell, vol. 9(1), p 54 to 63, 2010.
NPL 10: Baraniak et al. Cell Tissue Res, vol. 347(3), p 701 to 711, 2012
NPL 11: Doetsch et al. Cell, 97 (6), p 703 to 716, 1999.
NPL 12: Laura et al. Protoc Exch, Doi:10.1038/nprot.2006.215, 2006

SEMINARY OF INVENTION

Technical Problem

An object to be achieved by the present invention is to culture MSCs for a long period of time while maintaining undifferentiation thereof.

Solution to Problem

Under such circumstances, the inventors of the present invention have made extensive investigations, and as a result, have found that, when MSCs are subjected to shaking culture, the MSCs can be led to form a cell construct and can be cultured for a long period of time while maintaining undifferentiation thereof. The present invention is based on such novel finding.

Therefore, the present invention provides a method and a cell construct as described in the following items.

Item 1. A method of culturing MSCs while maintaining undifferentiation thereof, the method including culturing MSCs by shaking culture.

Item 2. The method according to Item 1, wherein the culturing is performed by shaking culture at a rotational speed of from 20 rpm to 200 rpm, preferably from 60 rpm to 120 rpm, more preferably from 85 rpm to 95 rpm.

Item 3. The method according to Item 1 or 2, wherein the culturing is performed at an amplitude of from 10 mm to 40 mm, preferably from 25 mm to 40 mm, more preferably from 30 mm to 40 mm.

Item 4. The method according to any one of Items 1 to 3, further including passaging the MSCs 2 or more times.

Item 5. The method according to any one of Items 1 to 4, wherein the MSCs to be subjected to the shaking culture are cells that have lost an ability to differentiate into predetermined cells, and the ability to differentiate into predetermined cells is restored by the shaking culture.

Item 6. A cell construct, which is obtained by the method of any one of Items 1 to 5.

Item 7. A cell differentiation method including a step of culturing the cell construct of Item 6 in a differentiation induction medium.

Item 8. A cell construct differentiated into predetermined cells by the method of Item 7.

Advantageous Effects of Invention

According to the present invention, as a result of the shaking culture, the MSCs can be led to form a cell construct and can be cultured for a long period of time while maintaining undifferentiation thereof. In addition, according to the present invention, when MSCs that have lost a differentiation ability by being subjected to related-art adherent culture or the like for a long period of time are used, it is also possible to restore their differentiation ability by subjecting the MSCs to the shaking culture. In the field of stem cells, to which the present invention belongs, it has been considered that a physical stimulus rather induces differentiation. Therefore, the above-mentioned effect of the present invention that the undifferentiation can be maintained for a long period of time by subjecting the MSCs to the shaking culture is an unexpected one that cannot be predicted from the related art.

BRIEF DESCRIPTION OF DRAWINGS

FIG. 1 are photographs for showing the formation of cell constructs of mouse and human MSCs by shaking culture (2 months). Left of FIG. 1: mouse MSCs. Used after 12 adherent passages. Right of FIG. 1: human MSCs. Used after 6 adherent passages.

FIG. 3 are photographs for showing the mesodermal differentiation ability of Oricell™ mouse MSCs subjected to shaking culture. Left column of FIG. 3: osteoblasts. Central column of FIG. 3: chondrocytes. Right column of FIG. 3: adipocytes. Upper row of FIG. 3: 1 month of shaking culture after 9 adherent passages. Lower row of FIG. 3: 1 month of shaking culture after 30 adherent passages.

FIG. 4 are photographs for showing gene expression analysis (RT-PCR) after differentiation induction into mesodermal cells. FIG. 4a: after bone differentiation induction. FIG. 4b: after cartilage differentiation induction. FIG. 4c: after fat differentiation induction. Numbers above FIG. 4a, FIG. 4b, and FIG. 4c each represent an adherent passage number (number of passages).

FIG. 6 are photographs for showing the cartilage differentiation ability of human MSCs. Upper row of FIG. 6a: cartilage (toluidine blue staining). 9 adherent passages. Lower row of FIG. 6a: cartilage (toluidine blue staining). Shaking culture after 9 adherent passages. Upper row of FIG. 6b: cartilage (toluidine blue staining). 19 adherent passages. No cartilage pellets formed. Lower row of FIG. 6b: cartilage (toluidine blue staining). Shaking culture after 19 adherent passages.

FIG. 7 are photographs for showing the results of adherent culture of MSC cell constructs using a three-dimensional suspension culture vessel of the related art.

FIG. 8 are photographs for showing differentiation ability analysis of Oricell™ mouse MSC cell constructs using a three-dimensional suspension culture vessel (related art).

FIG. 9 are photographs for showing the morphology retention and cell supply ability of a human MSC cell construct subjected to shaking culture. First from left of upper row of FIG. 9a: The cell construct is seeded in an adherent culture dish, 0 days. Second from left of upper row of FIG. 9a: 1 day. Third from left of upper row of FIG. 9a: 7 days. Fourth and fifth from left of upper row of FIG. 9a: readhesion of cell construct (first time). First from left of middle row of FIG. 9a: 12 days. Second from left of middle row of FIG. 9a: 15 days. Third from left of middle row of FIG. 9a: 27 days. Fourth from left of middle row of FIG. 9a: 44 days. Fifth from left of middle row of FIG. 9a: 54 days. Left of lower row of FIG. 9a: 57 days. Right of lower row of FIG. 9a: 67 days. FIG. 9b: Migratory cells after a third time of readhesion are induced to differentiate (Left of FIG. 9b: osteoblasts. Right of FIG. 9b: adipocytes).

FIG. 10 are a graph and photographs for showing a cell construct formed by shaking culture of purified mouse MSCs. Right of FIG. 10a: purified mouse MSCs. FIG. 10b: day 1 of adhesion. Adipocytes (adiposomes) after differentiation induction are shown in FIG. 10c.

FIG. 11 are photographs for showing the formation of a cell construct of Oricell™ mouse MSCs using neural stem cell medium. FIG. 11a: 1 month of shaking culture after 9 adherent passages. FIG. 11b: 1 month of shaking culture after 9 adherent passages (First from left of FIG. 11b: bone differentiation. Second from left of FIG. 11b: fat differentiation. Third from left of FIG. 11b: cartilage differentiation.) FIG. 11c: Neural differentiation. FIG. 11d: 1 month of shaking culture after 39 adherent passages. FIG. 11e: RT-PCR after 1 month of shaking culture (numbers above FIG. 11d represent passage numbers)

DESCRIPTION OF EMBODIMENTS

Figure 2A:
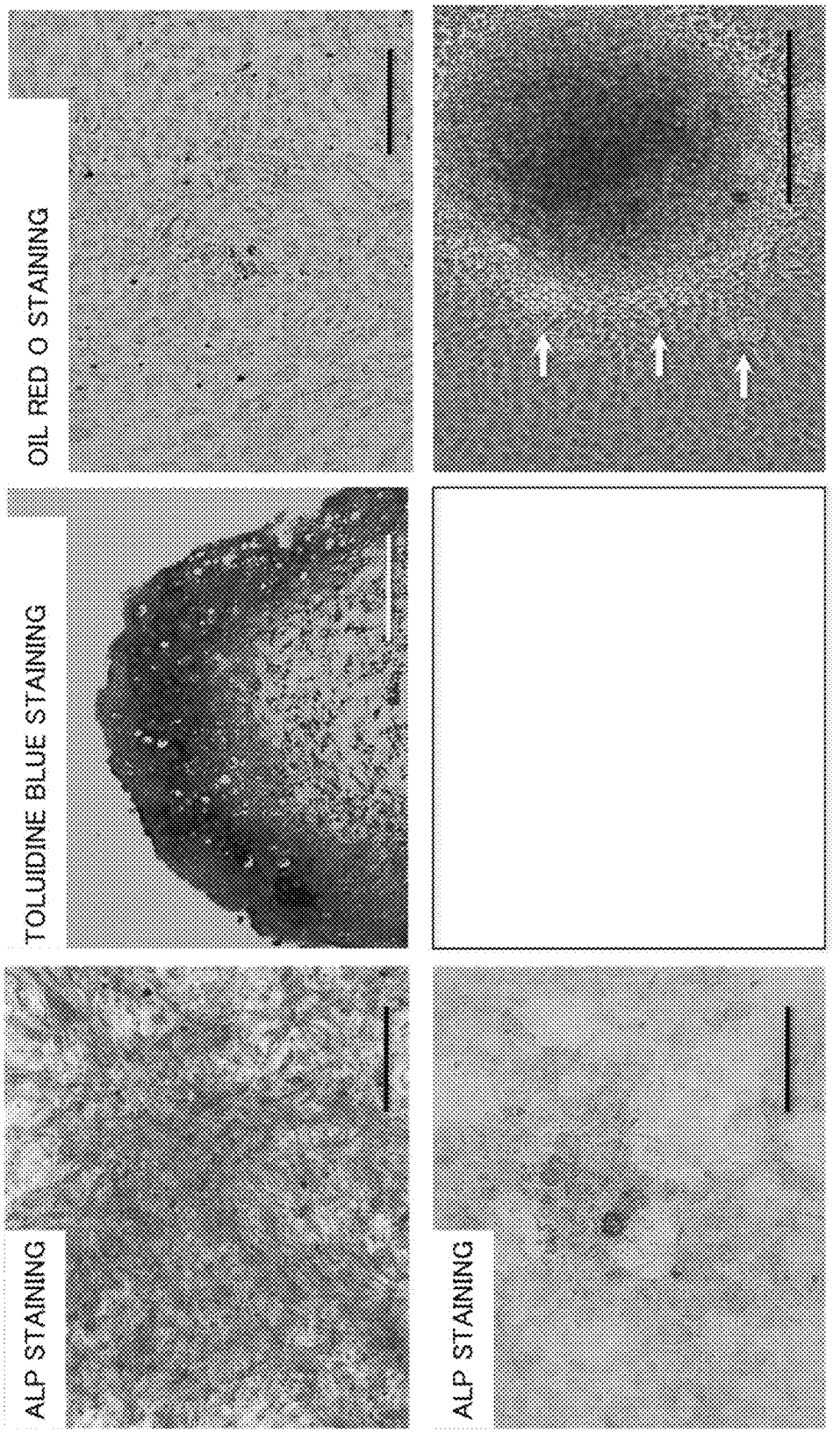
FIG. 2 are photographs and graphs for showing the influence of shaking culture on the maintenance of the differentiation ability of mouse MSCs. Upper row of FIG. 2a: 11 adherent passages (left of upper row of FIG. 2a: osteoblasts, center of upper row thereof: chondrocytes, right of upper row thereof: adipocytes). Lower row of FIG. 2a: shaking culture after 36 adherent passages (left of lower row of FIG. 2a: osteoblasts, right of lower row: adipocytes). Left of FIG. 2b: 8 adherent passages. Right of FIG. 2b: shaking culture after 44 adherent passages.
FIG. 2c: PDGFRα expression analysis (RT-PCR) of cell constructs subjected to 9, 25, and 41 adherent passages and 2 months of shaking culture after 11 and 37 adherent passages.

Method of Culturing MSCs while Maintaining Undifferentiation

The present invention provides a method of culturing MSCs as a cell construct while maintaining undifferentiation thereof, the method including subjecting MSCs to shaking culture.

The kind of the MSCs to be used in the present invention is not particularly limited, and examples thereof include bane marrow-derived cells, dental pulp-derived cells, and fat tissue-derived cells. In addition, the animal species of the MSCs is also not particularly limited, and examples thereof include MSCs derived from mammals, such as primates (e.g., humans and monkeys, preferably humans) and rodents (e.g., mice, rats, and rabbits).

The present invention has a feature in subjecting such MSCs to shaking culture. A culture vessel is not particularly limited, and may be appropriately set in accordance with, for example, the amount of culture medium to be needed and the kind of shaking method. Examples of the shape of the culture vessel include an Erlenmeyer flask and such a flask for a seesaw bioreactor as illustrated in the drawings of WO 2015/064705 A1 (e.g., a flask whose bottom surface is polygonal (tetra- to octagonal)). The capacity of the culture vessel is, for example, from 125 ml to 3,000 ml, preferably from 125 ml to 500 ml. As the culture vessel, a non-adherent culture vessel subjected to such a treatment that the adhesion of cells to the bottom surface or the like of the inner wall of the vessel is suppressed (e.g., a nan-adherent culture dish, a non-adherent well, or a non-adherent flask) may be used, or a general culture vessel that has not been particularly subjected to such treatment may be used.

The kind of the shaking method is also not particularly limited, and examples thereof include rotary, figure-eight, reciprocating, and seesaw types. In the present invention, the rotary type is preferred, but any other mode of shaking may be adopted. In the case of rotary shaking culture, a rotational speed is not particularly limited, but may be typically set within the range of, for example, from 20 rpm to 200 rpm, preferably from 60 rpm to 120 rpm, more preferably from 85 rpm to 95 rpm. A case in which the shaking culture is performed within the above-mentioned range of the rotational speed is preferred because both the side surface and bottom surface (bottom) of the inside of the culture vessel become less liable to have spheres adhering thereto.

Herein, the shaking conditions, such as the rotational speed and the amplitude, have been described by taking the rotary type as an example of a preferred embodiment. However, as long as a physical stimulus similar to that applied under the above-mentioned conditions can be applied to the stem cells, the figure-eight type, the reciprocating type, the seesaw type, or the like may be adopted. For example, in the case of the figure-eight shaking culture, the culture vessel is shaken so as to follow an orbit made up of two substantially circular shapes touching each other at one point, and hence conditions may be set so that the rotational speed and amplitude exemplified in the above-mentioned rotary type are achieved for each of the circles forming the figure eight. In addition, for example, in the case of the reciprocating type, the number of reciprocations per minute and the amplitude may be appropriately set within the ranges of from 20 reciprocations/min to 250 reciprocations/min and from 10 mm to 40 mm, respectively. For example, in the case of the seesaw type, the angle of the shaking culture and the cycle of shaking may be appropriately set within the ranges of from 2° to 12° and from 5 rpm to 60 rpm, respectively.

A medium to be used is not particularly limited as long as the medium is a liquid medium suitable for the culture of stem cells. An example of such medium is a minimum essential medium (MEM). The medium may contain an additive to be incorporated in general culture of stem cells as required. Specific examples of the additive include fetal bovine serum, amino acids (e.g., L-glutamine and L-alanyl-L-glutamine), and antibiotics (e.g., penicillin and streptomycin).

As a preferred mode of the culture of the present invention, there is given passaging. In the passaging, the stem cells are collected before reaching a confluent state, and for example, in the case of MSCs, the cells are seeded in a fresh medium at from about $1\times10^3$ cells/ml to about $1\times10^7$ cells/ml, preferably from about $1\times10^5$ cells/ml to about $1\times10^6$ cells/ml. In addition, in the culture of the present invention, it is preferred that the medium be changed appropriately (e.g., every 1 to 5 days, preferably every 3 to 4 days). According to the method of the present invention, the MSCs can be passaged in an undifferentiated state without losing their differentiation ability. In the present invention, the passaging may be performed by shaking culture, for example, 1 or more times, preferably 3 or more times, more preferably 5 or more times. In addition, in the present invention, the upper limit of the passaging by shaking culture is also not particularly limited, but the passaging may be performed, for example, 3 or less times, preferably 2 or less times, more preferably 1 or less times.

The period of time of the shaking culture is, for example, preferably from about 1 day to about 90 days (about 24 hours to about 2,160 hours), more preferably from about 10 days to about 75 days (about 240 hours to about 1,800 hours), still more preferably from about 14 days to about 60 days (about 336 hours to about 1,440 hours). A shaking culture temperature in this step is not particularly limited, and is, for example, preferably from 30° C. to 42° C., more preferably from 35° C. to 39° C. Such culture is preferably performed under an atmosphere of 3% to 10% $CO_2$.

By such method of the present invention, the MSCs can be cultured while including ones in an undifferentiated state and in a state of having a differentiation ability. In addition, as a result of the shaking culture, the MSCs grow and aggregate to form a cell construct. Therefore, with regard to the culture of MSCs, the present invention also provides: a method of forming a (undifferentiated) cell construct, including subjecting MSCs to shaking culture; a method of suppressing differentiation of MSCs, including subjecting MSCs to shaking culture; and the like. The cell construct obtained by the method of the present invention has an ability to differentiate into various cells belonging to the category of mesodermal cells, and in a preferred embodiment, the cell construct has an ability to differentiate into osteoblasts, adipocytes or the like, or chondrocytes, more preferably adipocytes or the like. As described in Examples, in related-art adherent culture, the ability to differentiate into adipocytes is lost, and hence such embodiment is preferred.

In the present invention, the "undifferentiation" means that the cells are in an undifferentiated state and have the differentiation ability. In the present invention, the undifferentiation of the MSCs may be typically confirmed on the basis of, for example, whether or not, as described in Examples of the present application, the MSCs show an ability to differentiate into both osteoblasts and adipocytes. In addition, in the present invention, the "maintenance of undifferentiation" encompasses not only a state in which the original differentiation ability of the MSCs is maintained without being lost, but also a state in which, although an ability to differentiate into at least one kind of cells (such as described above) into which the MSCs can originally differentiate was reduced or lost once during a culture process previous to the shaking culture, the differentiation ability has been restored through the shaking culture. Therefore, in the present invention, the scope of the "maintenance of undifferentiation" also encompasses, for example, a state in which, as described in Examples of the present application, through shaking culture of MSCs that have lost an ability to differentiate into predetermined cells (e.g., adipocytes) as a result of repeated passaging by a method other than the shaking culture (e.g., adherent culture), the ability to differentiate into the cells has been restored. Therefore, in such embodiment, the present invention also provides a method of restoring an ability to differentiate into predetermined cells, including subjecting MSCs that have lost the ability to differentiate into the predetermined cells to shaking culture.

In addition, the method of the present invention has a feature in subjecting MSCs to shaking culture, but static culture may be combined therewith as long as the effect of the present invention is obtained. For example, as described in Examples of the present application, after a cell construct retaining undifferentiation has been formed through the shaking culture for a given period of time, such cell construct may be subjected to the static culture. Such static culture may be performed by adherent culture, or may be performed by non-adherent culture. For a medium, a culture temperature, a $CO_2$ concentration, and the like in such static culture, conditions similar to those for the shaking culture described above may be appropriately adopted. As a culture vessel, a non-adherent culture vessel subjected to such a treatment that the adhesion of cells to the bottom surface and the like of the inner wall of the vessel is suppressed (e.g., a non-adherent culture dish, a non-adherent well, or a non-adherent flask) may be used, or a general culture vessel that has not been particularly subjected to such treatment may be used. The number of passages in the static culture is not particularly limited as long as the effect of the present invention is obtained, but for example, in the present invention, the passaging may be performed 2 or more times, preferably 3 or more times, more preferably 5 or more times. In addition, when the static culture is performed, the upper limit of the passaging in the static culture is also not particularly limited, but the passaging may be performed, for example, 5 or less times, preferably 3 or less times, more preferably 1 or less times. In such embodiment, the period of time of the static culture is, for example, preferably from about 0.1 day to about 60 days, more preferably from about 1 day to about 30 days, still more preferably from about 3 days to about 14 days. That is, in such embodiment of the present invention, the period of time of the static culture is, for example, preferably from about 2.4 hours to about 1,440 hours, more preferably from about 24 hours to about 720 hours, still more preferably from about 72 hours to about 336 hours.

Cell Construct Retaining Undifferentiation

The present invention provides a cell construct obtained by the above-mentioned culture method of the present invention. Herein, the "cell construct" means a construct of cells having a three-dimensional expanse, not a group of cells that have grown two-dimensionally along the bottom surface and/or wall surface of the inner wall of a culture vessel by adherent culture or the like. The cell construct may also be called a sphere, a spheroid, or the like. The cell construct of the present invention exhibits the following effect: the cell construct is in an undifferentiated state and has not lost its differentiation ability even after long-term culture. In this connection, in the present invention, all cells constituting the cell construct may maintain undifferentiation, but it is only required that the cell construct contain cells maintaining undifferentiation to the extent that the cell construct can be used in applications such as: use as a stem cell pool for continuously supplying stem cells retaining undifferentiation; and application to regenerative medicine.

It is apparent from Examples of the present application and the like that the effect that the cell construct according to the invention of the present application maintains undifferentiation even after long-term culture is one achieved by performing the above-mentioned shaking culture. However, it is extremely difficult to specify the features of such cell construct by expressing the structure or characteristics of the cell construct itself in words without using the description of the above-mentioned step.

In the description regarding the above-mentioned method of the present invention, the rotary shaking culture has been given as a preferred kind of shaking method in the shaking culture for obtaining the cell construct, but for example, the scope of the "cell construct obtained by the rotary shaking culture" in the present invention may naturally encompass not only a cell construct actually obtained by the rotary shaking culture, but also any cell construct subjected to shaking culture by any other method as long as the latter cell construct, like the former, is in an undifferentiated state and has not lost its differentiation ability.

In addition, for example, in the case of mouse MSCs, the cell construct of the present invention may be positive for a marker such as PDGFRα, Sca-1, or both thereof, preferably PDGFRα. In addition, for example, in the case of human MSCs, the cell construct of the present invention may be positive for a marker such as CD90 or CD106. Being positive for such marker means, for example, that, when measurement is performed in accordance with a method described in Examples of the present application, the ratio of a positive fraction in the cell construct is 50% or more.

Differentiation Induction Method

The present invention provides a cell differentiation method including a step of culturing the above-mentioned cell construct of the present invention in a differentiation induction medium.

By the method of the present invention, differentiation from MSCs into cells belonging to the category of mesodermal cells can be induced. Examples of the cells belonging to the category of mesodermal or mesenchymal cells include adipocytes, osteoblasts, chondrocytes, bone cells, cardiomyocytes, tendon cells, pulp cells, and odontoblasts, and preferred examples thereof include osteoblasts and adipocytes. In addition, the cell construct of the present invention is also applicable to the culture of purified MSCs including neural crest-derived cells (Non-patent Literature 4), and examples thereof include cells belonging to the neural crest, such as neuronal cells, glial cells, smooth muscle cells, pulp cells, odontoblasts, cementoblasts, and periodontal ligament cells (preferably neuronal cells and odontoblasts, more preferably neuronal cells).

As a medium to be used in this step, a medium suitable for the induction of differentiation into cells of a desired kind may be appropriately used. Examples of such medium include: DMEM medium (e.g., sodium pyruvate-free DMEM medium manufactured by Nacalai Tesque Inc.); αMEM medium (e.g., MEM Alpha (1×) medium manufactured by Gibco); Mesenchymal stem cell growth medium manufactured by Takara Bio Inc.; and MSCGM™ Mesenchymal stem cell growth medium, hMSC-Human Mesenchymal Stem cell Osteogenic Differentiation Medium Bullk-Kit™, hMSC-Human Mesenchymal Stem cell Chondrogenic Differentiation Medium BullkKit™, and hMSC-Human Mesenchymal Stem cell Adipogenic Differentiation Medium BullkKit™ manufactured by LONZA. Those media may be used alone or in combination thereof.

In this step, an agent for promoting the induction of differentiation into cells of a desired kind and the like may be blended into the medium.

Examples of the agent for promoting the induction of differentiation into adipocytes include insulin, dexamethasone, and 3-isobutyl-1-methylxanthine. Those agents for promoting the induction of differentiation into adipocytes may be used alone or in combination thereof.

Examples of the agent for promoting the induction of differentiation into osteoblasts include: compounds such as ascorbic acid, ascorbic acid 2-phosphate, β-glycerophosphoric acid, dexamethasone, hydrocortisone hemisuccinate, statin, an isoflavone derivative, a 3-benzothiepine derivative TAK-778 ((2R,4S)-(–)-N-[4-(diethoxyphosphorylmethyl)phenyl]-1,2,4,5-tetrahydro-4-methyl-7,8-methylenedioxy-5-oxo-3-benzothiepine-2-carbaxamide), a helioxanthin derivative TH (4-(4-methoxyphenyl)pyrido[40,30:4,5]thieno[2,3-b]pyridine-2-carboxamide), phenamil (3,5-di-amino-6-chloro-N-[imino(phenylamino)methyl]pyrazine-2-carboxamide), harmine and analogs thereof, acerogenin and analogs thereof, and resveratrol; and proteins involved in bone formation [e.g., bone morphogenic protein (BMP)-2, BMP-4, insulin-like growth factor (IGF)-1, basic fibroblast growth factor (βFGF), transforming growth factor (TGF)-β1, parathyroid hormone (PTH), and Wnts]. Those agents for promoting the induction of differentiation into osteoblasts may be used alone or in combination thereof.

Examples of the agent for promoting the induction of differentiation into chondrocytes include BMP-6, TGF-β3, dexamethasone, and ascorbic acid. Those agents for promoting the induction of differentiation into chondrocytes may be used alone or in combination thereof.

Examples of the agent for promoting the induction of differentiation into cardiomyocytes include KY03I, KY02111, and βFGF. Those agents for promoting the induction of differentiation into cardiomyocytes may be used alone or in combination thereof.

Examples of the agent for promoting the induction of differentiation into tendon cells include PDGF and VEGF. Those agents for promoting the induction of differentiation into tendon cells may be used alone or in combination thereof.

Cell Construct Induced to Differentiate

The present invention provides a cell construct differentiated into predetermined cells by the above-mentioned differentiation induction method of the present invention.

The cell construct induced to differentiate according to the present invention uses, as a source material, the undifferentiated cell construct obtained by the method of the present invention described above. As described above, the undifferentiated cell construct of the present invention serving as the source material is different from a related-art cell construct of MSCs, and exhibits the unpredictable effect of being in an undifferentiated state and having not lost its differentiation ability even after long-term passaging. Therefore, it is apparent that the cell construct induced to differentiate into desired cells using such undifferentiated cell construct as a source material is also different from the related-art cell construct.

Now, embodiments of the present invention are more specifically described by way of Examples, and the action and effect of the present invention are demonstrated. These Examples are for illustrative purposes and for specific description, and the present invention is not limited to these Examples.

EXAMPLES

Experimental Methods

Experiments were performed in accordance with the following methods.

Purification Sorting of Mouse MSCs (See Non-Patent Literature 6)

The femurs and tibias of five 4-week-old male C57/BL6 mice (CLEA JAPAN) were crushed with a mortar and pestle, and suspended in HBSS$^+$ (Cat. #14025134: Gibco) having added thereto 2% FBS (Cat. #SH30910.03: Hyclone), 10 mM HEPES (Cat. #346-01373: Dojindo), and 1% Penicillin/Streptomycin (P/S: Cat. #168-23191, Wako) (hereinafter referred to as HBSS$^+$ adjusting solution), and red blood cells were removed. The bone crushed to powder was enzymatically treated at 37° C. for 1 hour with a solution of 0.2% collagenase (Cat. #034-10533: Wako) in DMEM (Cat. #08459-64: Nacalai tesque) containing 10 mM HEPES (Cat. #346-01373: Dojindo) and 1% P/S (Cat. #168-23191: Wako). The enzymatically treated bone was passed through a cell strainer having a diameter of 40 μm (Cat. #352340: Falcon) and centrifuged at 280 G and 4° C. for 7 minutes. The supernatant was removed, and the cells were collected. Normally, $1 \times 10^7$ to $3 \times 10^7$ cells can be collected from one mouse. $1 \times 10^7$ of the collected cells were suspended in 1 ml of the HBSS$^+$ adjusting solution, and 2 μl each of PE-conjugated CD45 (30-F11: Cat. #12-0451-83, 0.2 mg/ml, eBioscience), TER119 (TER-119: Cat. #12-5921-83, 0.2 mg/ml, eBioscience), APC-conjugated PDGFRα (APA5: Cat. #17-1401-81, 0.2 mg/ml, eBioscience), and FITC-conjugated Sca-1 (Ly6A/E: Cat. #11-5981-85, 0.5 mg/ml, eBioscience) antibodies were added. The whole was left to stand still in an environment at 4° C. under light shielding for 30 minutes. Next, the resultant was centrifuged at 280 G and 4° C. for 7 minutes and adjusted with the HBSS$^+$ adjusting solution so as to be a cell suspension at $1 \times 10^7$ cells/1 ml. After dead cells had been labeled by staining with propidium iodide (PI: Cat. #169-26281, WAKO) at a final concentration of 1 μg/ml, PI$^-$/CD45$^-$/Ter119$^-$/PDGFRα$^+$/Sca-1$^+$ cells were sorted using Aria III flow-cytometer (BD Bioscience) (FIG. 6-a).

FACS Analysis of Mouse MSCs

Cell sample passaged by adherent culture: Cells subjected to adherent culture in a 10 cm culture dish (Cat. #664160-013: CELLSTAR) were washed twice with PBS, and then the cells were detached using 1 ml of cell dissociation buffer (Cat. #13151014: Gibco). The HBSS$^+$ adjusting solution was added, and the whole was centrifuged at 280 G and 4° C. for 5 minutes. The supernatant was removed, and the precipitated cells were collected.

Cell construct sample formed by shaking culture: In consideration of the difficulty in separating cell constructs into single cells for collection without damaging the cells of the cell constructs or their cell surface antigens, first, 10 cell constructs on average were left to stand still in 10 cm culture dishes (Cat. #664160-013: CELLSTAR) for 7 days, and cells that had migrated from the cell constructs adhering to the culture dishes were washed twice with PBS. After the removal of PBS, 1 ml of cell dissociation buffer (Cat. #13151014: Gibco) was added to the culture dishes and allowed to act for from 2 minutes to 3 minutes to detach the cells. Subsequently, 9 ml of the HBSS$^+$ adjusting solution was added, and the whole was centrifuged at 280 G and 4° C. for 5 minutes. The supernatant was discarded, and the precipitated cells were collected, $1 \times 10^7$ of the collected cells were suspended in 1 ml of the HBSS$^+$ adjusting solution, and 2 μl each of an APC-conjugated Sca-1 (Ly6A/E: Cat. #11-5981-85, 0.5 mg/ml, eBioscience) antibody was added. The whole was left to stand still in an environment at 4° C. under light shielding for 30 minutes. Next, the resultant was centrifuged at 280 G and 4° C. for 7 minutes and adjusted with the HBSS$^+$ adjusting solution so as to be a cell suspension at $1 \times 10^7$ cells/1 ml, which was analyzed using Aria III (BD Bioscience). In the analysis of cell construct-derived cells, passaging was not performed even once, and the cells that had migrated from the cell constructs were directly used for the analysis.

Purification Sorting of Provided Human MSCs (See Non-Patent Literature 7)

Human MSCs received from Tokyo Medical and Dental University are cells sorted from the femur bone marrow of a 19-year-old male with MoFlo (BECKMAN COULTER) using PE-conjugated CD271 (LNGFR: Cat. #130-091-885, Miltenyi Biotec) and FITC-conjugated CD90 (Thy-1: Cat. #328110, Biolegend) antibodies (Non-patent Literature 7). Cells that had been passaged twice after sorting of a negative fraction as living cells using PI for labeling dead cells were provided.

FACS Analysis of Human MSCs

As in the analysis of mouse cells, for adherent cells, cells cultured in a 10 cm culture dish (Cat. #664160-013: CELLSTAR) were washed twice with PBS, and the cells were detached using 1 ml of cell dissociation buffer (Cat. #13151014: Gibco). 9 ml of the HBSS$^4$ adjusting solution was added, and the whole was centrifuged at 280 G and 4° C. for 5 minutes. The supernatant was removed, and the cells were collected. In the analysis of cell constructs, 10 cell constructs on average were left to stand still in 10 cm culture dishes (Cat. #664160-013: CELLSTAR) for 7 days, cells that had migrated from the cell constructs adhering to the culture dishes were washed twice with PBS, and the cells were detached using 1 ml of cell dissociation buffer (Cat. #13151014: Gibco). 9 ml of the HBSS$^+$ adjusting solution was added, and the whole was centrifuged at 280 G and 4° C. for 5 minutes. The supernatant was removed, and the cells were collected. In the analysis of cell construct-derived cells, passaging was not performed even once, and the cells that had migrated from the cell constructs were directly used for the analysis. In both the case of adherent culture and the case of cell construct-derived adherent culture, $7 \times 10^6$ to $1 \times 10^7$ cells were able to be collected from one 10 cm culture dish, $1 \times 10^7$ of the collected cells were suspended in 1 ml of the HBSS$^+$ adjusting solution, and 2 μl each of (PE-conjugated LNGFR: Cat. #130-091-885, 5.5 μg/ml, Miltenyi Biotec), FITC-conjugated Thy-1: Cat. #328110, 0.2 mg/ml, Biolegend), and APC-conjugated CD106 (VCAM-1): Cat. #305810, 0.5 mg/ml, Biolegend) antibodies were added. The whole was left to stand still in an environment at 4° C. under light shielding for 30 minutes. Next, the resultant was centrifuged at 280 G and 4° C. for 5 minutes and adjusted with the HBSS$^+$ adjusting solution so as to be a cell suspension at $1 \times 10^7$ cells/1 ml, which was analyzed using Aria III (BD Bioscience).

Adherent Culture of Mouse and Human MSCs

OriCell™ Strain C57BL/6 mouse MSCs (MUBMX-01001: CYAGEN) and purified mouse MSCs were cultured using MEM-α+GlutaMAX-I (Cat. #32561-102: Gibco) containing 10% FBS (Cat. #SH30910.03: Hyclone), 1% P/S (Cat. #168-23191: Wako), and 10 mM HEPES (Cat. #346-01373: Dojindo) as a growth maintenance medium.

Human MSCs were cultured using DMEM (Cat. #08459-64: Nacalai tesque) containing 20% FBS (Cat. #SH30910.03: Hyclone), 1% P/S (Cat. #168-23191: Wako), 10 mM HEPES (Cat. #346-01373: Dojindo), and ng/ml βFGF (Cat. #064-05384: WAKO) as a growth maintenance medium.

The mouse or human MSCs were seeded in a 10 cm culture dish (Cat. #664160-013: CELLSTAR) at a concentration of $1 \times 10^6$ cells/dish, cultured under an environment of 5% $CO_2$ at 37° C. for from 4 days to 7 days, and passaged in an 80% confluent state. The passaging was performed in the following manner. The medium was aspirated, serum components were then removed with 1×PBS, and the cells were treated with 0.25% trypsin-EDTA (Cat. #201-16945: Wako) for 2 minutes. The dish was gently tapped, and when the cells began to be detached, the growth maintenance medium was immediately added, and the cells were collected. The cells were centrifuged at 250×g for 5 minutes, the growth maintenance medium was then added to the precipitated cells front which the supernatant had been removed by aspiration, and the cells were seeded in a fresh 10 cm culture dish at $1 \times 10^6$ cells/dish.

OriCell™ Strain C57BL/6 mouse MSCs (MUBMX-01001: Cyagen) are cells that have already been passaged 6 times by the manufacturer at the time of purchase. In addition, the cells to be purchased have been confirmed by the manufacturer to be CD29-, CD44-, CD31-, and Sca-1-positive (>70%) and CD117-negative (<5%) before shipping. In addition, the manufacturer recommends the use thereof at a passage number of 10 or less, and does not guarantee the properties that the cells have at the time of purchase for further passaging. In addition, the use of OriCell™ Mouse MSC Growth Medium (MUXMX90011: Cyagen) is recommended for maintenance culture of cells.

MSC Shaking Suspension Culture

TAITEC BR-40LF bio-shaker was used for shaking culture. A cell suspension of mouse or human MSCs adjusted with 20 ml of the growth maintenance medium was prepared in a 125 ml erlenmeyer flask (Cat. #431405: Corning). In the shaking culture of the mouse MSCs (OriCell™ mouse MSCs and purified mouse MSCs), the growth maintenance medium was supplemented with 20 ng/ml βFGF (Cat. #064-05384: WAKO. The numbers of cells per flask at the start of the shaking culture were adjusted to $1.0 \times 10^7$ for the OriCell™ mouse MSCs, $5.0 \times 10^5$ for the purified mouse MSCs, and $1.0 \times 10^6$ or $1.0 \times 10^7$ for the human MSCs. The shaking culture was performed under rotation at 37° C., 5% $CO_2$, from 85 r/min to 95 r/min, and an amplitude of 40 mm, and the medium was changed once every 3 to 4 days. The medium was changed as described below. First, the entire medium including the cells was transferred to a 50 ml centrifuge tube (Cat. #TR2004: True Line) and centrifuged at 280 G and 4° C. for 5 minutes. After the removal of the supernatant, 20 ml of fresh medium was added using a 25 ml pipette (Cat. #760180: greiner bio-one), and the whole was subjected to pipetting 2 or 3 times and transferred to the flask. After 10 days to 14 days from the start of the shaking culture, the formation of cell constructs was able to be macroscopically confirmed.

Mouse MSC Shaking Suspension Culture Using Neural Stem Cell Medium

Advanced DMEM/F12 (Cat. 12491015: Gibco) containing 1% P/S (Cat. #168-23191: Wako) and 10 mM HEPES (Cat. #346-01373: Dojindo), 1×N2 (Cat. #17502-048: Gibco), 20 ng/ml EGF (Cat. #059-07873: WAKO), 20 ng/ml FGF (Cat. #064-05384: WAKO), and 1×B27 (Cat. #17504-044: Gibco) was used as a neural stem cell medium (see Non-patent Literature 4, Non-patent Literature 11, and Non-patent Literature 12).

A cell suspension of mouse MSCs (Oricell™ mouse MSCs: 1.0×107 cells) was adjusted with 20 ml of the neural stem cell medium, and prepared in a 125 ml erlenmeyer flask (Cat. #431405: Corning). The cell suspension was subjected to shaking culture while being rotated at 37° C., 5% $CO_2$, from 85 r/min to 95 r/min, and an amplitude of 40 mm through the use of TAITEC BR-40LF bio-shaker. The medium was changed once every 3 to 4 days. The medium was changed as described below. First, the entire medium including the cells was transferred to a 50 ml centrifuge tube (Cat. #TR2004: True Line), and the cells were centrifuged at 280 G and 4° C. for 5 minutes. After the removal of the supernatant, 20 ml of fresh medium was added using a 25 ml pipette (Cat. #760180: Greiner bio-one), and the whole was subjected to pipetting 2 or 3 times and transferred to the flask. After 10 days to 14 days from the start: of the shaking culture, the formation of cell constructs was macroscopically confirmed.

Formation of MSC Cell Constructs Using Existing Three-Dimensional Suspension Culture Vessel The mouse or human MSCs subjected to the adherent culture were seeded in a Kuraray three-dimensional culture vessel (Elplasia Cat. #FB 500 400 NA Plate: Kuraray) at a suspended cell concentration of 3×10$^6$ cells/ml. For culture, the same growth maintenance medium as that in the MSC shaking suspension culture described above was used, and the medium was changed once every 3 to 4 days.

Readhesion and Cell Expansion of MSC Cell Constructs

The cell constructs formed by subjecting the mouse or human MSCs to the shaking culture were left to stand still in a plastic culture dish containing the growth maintenance medium to be caused to adhere thereto. At this time, for the human MSCs, a medium obtained by removing βFGF from the above-mentioned growth medium was used. As a result, cell expansion of the mouse and human MSCs was able to be achieved. Many cells migrated from the peripheries of the cell constructs adhering to the culture dish, and expanded to spread over the culture surface of the culture dish. After the migration and expansion of the cells, the main bodies of the cell constructs adhering to the culture dish were able to be easily collected by stripping the bottom surfaces of the cell constructs using the end of a 200 µl pipette tip. When the collected cell constructs were again left to stand still in another culture dish, cell expansion by similar cell migration was able to be achieved. Cells that had been allowed to migrate and expand in a 10 cm culture dish (Cat. #664160-013: CELLSTAR) or a 12-well plate (Cat. #665-180: CELLSTAR) were respectively used for Frow-cytometry analysis or differentiation induction analysis. In the differentiation induction analysis, 2 or 3 cell constructs were seeded in each well of the 12-well plate (see Differentiation Induction Method). In culture in the 10 cm culture dish, 8 to 12 cell constructs each having a diameter of more than 200 µm were left to stand still so as to keep uniform distances across the entirety of the culture dish.

Differentiation Induction Method and Staining Method (See Non-Patent Literature 6)

Differentiation induction into osteoblasts and adipocytes was performed by seeding cells in a 12-well plate (Cat. #665-180: CELLSTAR) at a concentration of 1×10$^5$ cells/well in the case of adherent culture. In the case of cell construct-derived migratory cells, 2 or 3 cell constructs were seeded in each well of a similar 12-well plate, and cells that had migrated and expanded from the cell constructs were used. After the seeding, the adhesion state of the cells was confirmed, and the medium was changed to osteoblast differentiation induction medium (Cat. #PT3002: Lonza) and adipocyte differentiation induction medium (Cat. #PT3004: Lonza) under a 60% to 70% confluent state (about 7 days of culture). Thereafter, differentiation induction was performed for up to 21 days while the medium was changed once every 3 to 4 days. In some cases, adherent cells and formed adiposomes were suspended and detached in about 2 weeks during the induction period. In those cases, culture was ended at that point of time. Alkaline phosphatase (ALP) staining was used for the confirmation of osteoblast differentiation, and Oil Red O staining was used for the confirmation of adipocyte differentiation. In each of the staining methods, hematoxylin staining was not performed.

For the induction of differentiation into chondrocytes, cells were allowed to form pellets in a 15 ml centrifuge tube at 150 G, and culture was performed using chondrocyte induction medium (Cat. #PT3003: Lonza) supplemented with 10 ng/ml transforming growth factor-03 (Cat. #PT4124: LONZA) and 500 ng/ml bone morphogenetic protein-6 (Cat. #6325-BM-020; R&D Systems). The medium was changed twice a week, and culture was performed for 21 days. The differentiation of induced chondrocytes was confirmed by toluidine blue staining (Cat. #209-14545: Wako). Hematoxylin staining was not performed.

All the stained cells were fixed using 4% paraformaldehyde (PFA) (Cat. #163-20145: Wako).

ALP Staining (See Non-Patent Literature 6)

Histofine assay Kit (Cat. #415161: Nichirei) was used for staining. PFA was washed with PBS, reagents in the kit were mixed and adjusted immediately before staining, and staining was performed for 30 minutes with a staining solution that had been filtered through a syringe filter having a pore size of 0.22 µm (Cat. #SLGP033RS: Merk Millipore), followed by water washing. As a negative control (NC), one obtained by simultaneously subjecting MSCs before osteoblast differentiation induction to ALP staining was used.

Oil Red O Staining (See Non-Patent Literature 6)

PFA was washed with PBS, and then treated with 60% isopropyl alcohol for 1 minute, followed by staining for 30 minutes with an Oil Red O staining solution (Cat. #40492: Muto Pure Chemicals) that had been filtered through a syringe filter having a pore size of 0.22 µm (Cat. #SLGP033RS: Merk Millipore). After the staining, the staining solution was removed, and treatment with 60% isopropyl alcohol was performed again for 1 minute, followed by water washing.

Toluidine Blue Staining (See Non-Patent Literature 6)

Cell pellets after differentiation induction were embedded in paraffin, and a section was produced on a slide glass. Paraffin removal with xylene and xylene removal with 100% alcohol were performed, and the resultant was treated with 80% alcohol, followed by staining for 30 minutes with a toluidine blue staining solution (Cat. #209-14545: Wako)

that had been filtered through a syringe filter having a pore size of 0.22 μm (Cat. #SLGP033RS: Merk Millipore). After the staining, the resultant was dehydrated with 100% alcohol, subjected to xylene treatment, and then mounted with Marinol (Cat. #2009-3: Muto pure Chemicals).

Neuronal Cell Induction (See Non-patent Literature 4)
Cell constructs subjected to shaking culture in the neural stem cell medium were transferred to a medium obtained by removing EGF, FGF, and 1×B27 from the neural stem cell medium and adding 10% FBS (Cat. #SH30910.03: Hyclone), and were treated with poly-L-omithine (Cat. #163-27421: WAKO; 37° C., 12 hours), followed by seeding in a chamber slide (Cat. #SCS-NO8: MATSUNAMI) that had been treated with fibronectin (Cat. #062-05701: WAKO; 37° C., 12 hours) (2 or 3 cell constructs/well). After 7 days from the seeding, cells that had migrated from the cell constructs were fixed using 4% PFA (Cat. #163-20145: WAKO), and were used for immunofluorescence staining observation.

Immunofluorescence Staining (See Non-Patent Literature 4)
The sample fixed with PEA was washed with 1×PBS, then treated using 0.3% Triton-X100 (Cat. #160-24751: WAKO) at room temperature for 5 minutes, and washed again with 1×PBS. The washed cells were treated with blocking buffer (0.01% Triton-X100 (Cat. #160-24751: WAKO), 1×PBS having added thereto 5% bovine serum albumin (Cat. #23208: Thermoscientific)) for 30 minutes, and then subjected to primary staining (4° C., overnight) with a 500-fold diluted anti-βIII-Tublin antibody (Cat. #ab18207: abcom). After that, the cells were washed with 1×PBS, and subjected to secondary staining (room temperature, 1 hour) with 1,000-fold diluted Donkey Anti-Rabbit IgG H&L (Alexa Flour (trademark) 488; Cat #ab150073: abcom). The cell sample was washed with 1×PBS, mounted using VECTASHIELD mounting medium with DAPI (Cat #H-1200: VECTOR), and observed using a confocal laser scanning microscope (LSM780: Zeiss).

RT-PCR
For total RNA extraction, Trizol (Cat. #15596108: Invitrogen) and RNeasy Mini Kit (Cat. #74106: Quiagen) were used (extraction was performed in accordance with the Quiagen Kit protocol), and genomic DNA was removed with DNase I (Cat. #AM2222: Antbion). For reverse transcription reaction, Reverse Transcription System (Cat. #A3500: Promega) was used, and random primers (Cat. #C118B: Promega), AMV reverse transcriptase (Cat. #M900B: Promega), and MgCl2 (Cat. #A351H: Promega) were used in accordance with the protocol procedure. In PCR reaction, cDNA was amplified using Go Taq Green Master Mix (Cat. #M7123: Promega) (in accordance with the Promega protocol procedure). PCR products were electrophoresed on 1.0 to 1.5% agarose gel:

```
Mouse
PDGFRα; 270 bp, 60° C., 35 cycles
F:
                                           (SEQ ID NO: 1)
5'-TACATCATCCCCCTGCCAGA-3'

R:
                                           (SEQ ID NO: 2)
5'-AAGGTTATCCCGAGGAGGCT-3'

GAPDH; 418 bp, annealing: 67° C., 26 cycles
F:
                                           (SEQ ID NO: 3)
5'-CACCATGGAGAAGGCCGGGG-3'

R:
                                           (SEQ ID NO: 4)
5'-GACGGACACATTGGGGGTAG-3'

OPN; 437 bp, 62° C. 35 cycles
F:
                                           (SEQ ID NO: 11)
5'-TCACCATTCGGATCAGTCTG-3'

R:
                                           (SEQ ID NO: 12)
5'-ACTTGTGGCTCTGATGTTCC-3'

OCN; 292 bp, 62° C., 35 cycles
F:
                                           (SEQ ID NO: 13)
5'-AAGCAGGAGGGCAATAAGGT-3'

R:
                                           (SEQ ID NO: 14)
5'-AGCTGCTGTGACATCCATAC-3'

Adipsin; 433 bp, 64° C., 40 cycles
F:
                                           (SEQ ID NO: 15)
5'-ACTCCCTGTCCGCCCCTGAACC-3'

R:
                                           (SEQ ID NO: 16)
5'-CGAGAGCCCCACGTAACCACACCT-3'

PPARγ; 460 bp, 56° C., 35 cycles
F:
                                           (SEQ ID NO: 17)
5'-GTGCGATCAAAGTAGAACCTGC-3'

R:
                                           (SEQ ID NO: 18)
5'-CCTATCATAAATAGCTTCAATCG-3'

Agrican; 146 bp, 64° C., 35 cycles
F:
                                           (SEQ ID NO: 19)
5'-CGCCACTTTCATGACCGAGA-3'

R:
                                           (SEQ ID NO: 20)
5'-TCATTCAGACCGATCCACTGGTAG-3'

SOX9; 132 bp, 61° C., 35 cycles
F:
                                           (SEQ ID NO: 21)
5'-CCTTCAACCTTCCTCACTACAGC-3'

R:
                                           (SEQ ID NO: 22)
5'-GGTGGAGTAGAGCCCTGAGC-3'

Col2A2; 121 bp, 61° C., 35 cycles
F:
                                           (SEQ ID NO: 23)
5'-CCTCCGTCTACTGTCCACTGA-3'

R:
                                           (SEQ ID NO: 24)
5'-ATTGGAGCCCTGGATGAGCA-3'

Nestin; 492 bp, 60° C., 35 cycles
F:
                                           (SEQ ID NO: 25)
5'-AATGGGAGGATGGAGAATGGAC-3'

R:
                                           (SEQ ID NO: 26)
5'-TAGACAGGCAGGGCTAGCAAG-3'

Twist; 225 bp, 64° C., 35 cycles
F:
                                           (SEQ ID NO: 27)
5'-CGAGGATGGAGGGGGCCTGG-3'
```

-continued

R:
(SEQ ID NO: 28)
5'-TGTGCCCCACGCCCTGATTC-3'

Human
Sox2; 151 bp, 64° C., 40 cycles
F:
(SEQ ID NO: 5)
5'-GGGAAATGGGAGGGGTGCAAAAGAGG-3'

R:
(SEQ ID NO: 6)
5'-TTGCGTGAGTGTGGATGGGATTGGTTG-3'

Oct3/4: 144 bp, 68° C., 40 cycles
F:
(EQ ID NO: 7)
5'-GACAGGGGGAGGGGAGGAGCTAGG-3'

R:
(SEQ ID NO: 8)
5'-CTTCCCTCCAACCAGTTGCCCCAAAC-3'

GAPDH; 613 bp, 56° C., 35 cycles
F:
(SEQ ID NO: 9)
5'-GTCAAGGCCGAGAATGGGAA-3'

R:
(SEQ ID NO: 10)
5'-GCTTCACCACCTTCTTGATG-3

Results

FIG. 1: Formation of Cell Constructs of Mouse and Human MSCs by Shaking Culture

The OriCell™ mouse MSCs (MUBMX-01001: Cyagen) and the human MSCs (MSCs purified from the bone marrow of a 19-year-old male) were repeatedly passaged by adherent culture to prepare cells having a small passage number and cells having a large passage number, which were subjected to shaking culture. The mouse MSCs were able to be passaged by adherent culture up to 50 times after purchase (56 times as counted from before shipping). The human MSCs were able to be passaged by adherent culture 20 times after provision (22 times as counted from before provision).

$1.0 \times 10^6$ of the mouse MSCs (total passage number including passages before shipping: 12) or $1.0 \times 10^7$ of the human MSCs (total passage number including passages before provision: 6) were prepared in a flask and subjected to shaking culture for 2 months. As a result, both the mouse and human MSCs formed cell constructs (FIG. 1). In addition, under the same shaking culture conditions, mouse MSCs having a passage number including passages before shipping of 44 and human MSCs having a passage number including passages before provision of 22 were used and subjected to shaking culture for 2 months. As a result, both the mouse and human MSCs formed cell constructs (not shown).

As described above, the OriCell™ mouse MSCs used herein had already been passaged 6 times by the manufacturer at the time of purchase, and the human MSCs had already been passaged twice at the time of provision. In Examples of the present invention, passage numbers to be hereinafter shown are counted numbers continuing from before shipping and from before provision (numbers including passage numbers before shipping and before provision).

When the number of cells at the start of the shaking culture was $1.0 \times 10^4$, the numbers of cell constructs formed by the human MSCs (passage number: 6 or 7) through the shaking culture were 14.3±2.0 after 1 month and 10.7±2.1 after 2 months. When the number of cells at the start of the shaking culture was $1.0 \times 10^7$, the numbers of cell constructs were 15.0±1.0 after 1 month and 11.7±2.5 after 2 months (mean±standard deviation for the results of three experiments). That is, even when the number of cells at the start of the shaking culture was increased 10-fold from $1.0 \times 10^5$, there was no significant difference in number of cell constructs formed.

When the number of cells at the start of the shaking culture was $1.0 \times 10^6$, the sizes of the cell constructs formed by the human MSCs having a passage number of 7 through the shaking culture were 433.3±103.3 μm at 1 month and 533.3±150.6 μm at 2 months. When the number of cells at the start of the shaking culture was $1.0 \times 10^7$, the sizes of the cell constructs were 783.3±248.3 μm after 1 month and 833.3±186.1 μm after 2 months (mean±standard deviation for the results of six experiments).

The numbers of cell constructs formed by the human MSCs having a large passage number (19 times) through 1 month of shaking culture were 14 and 15 when the numbers of cells at the start of the shaking culture were $1.0 \times 10^6$ and $1.0 \times 10^7$, respectively (results of one experiment). In addition, the sizes of the cell constructs formed by the human MSCs having a passage number of 19 through 1 month of shaking culture were 500±126.5 μm and 766.7±206.6 μm when numbers of cells at the start of the shaking culture were $1.0 \times 10^6$ and $1.0 \times 10^7$, respectively (mean±standard deviation of 6 cell constructs).

Figure 2C:
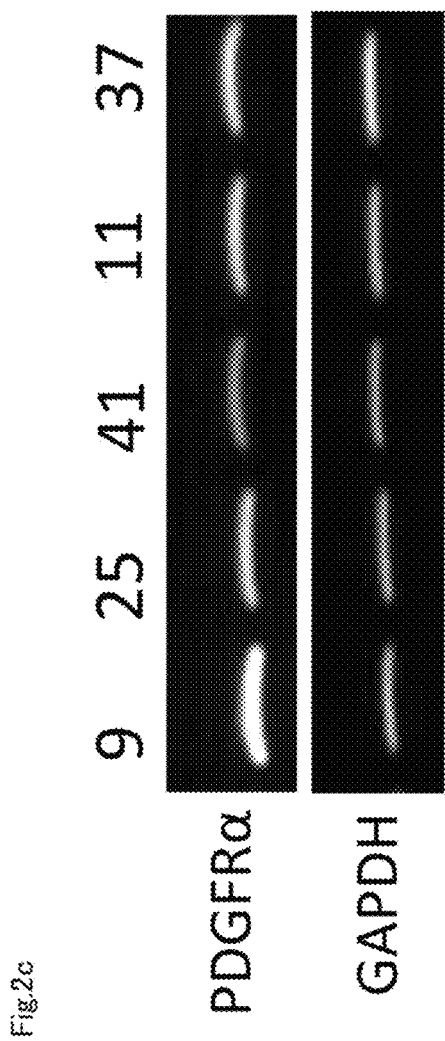

FIG. 2: Influence of Shaking Culture on Maintenance of Differentiation Ability of Mouse MSCs The influence of shaking culture on the maintenance of the differentiation ability of mouse MSCs was investigated. In adherent culture, the OriCell™ mouse MSCs maintained an ability to differentiate into osteoblasts (ALP staining-positive) and an ability to differentiate into chondrocytes (toluidine blue staining-positive) at a relatively small passage number of 11, but had already lost an ability to differentiate into fat, thus being negative for Oil Red O staining (FIG. 2-a: upper row).

However, when even OriCell™ mouse MSCs repeatedly passaged many times (36 times) by adherent culture were subjected to shaking culture for 2 months to form cell constructs, cells that had migrated and grown from the cell constructs retained or restored not only an ability to differentiate into osteoblasts (ALP staining-positive), but also an ability to differentiate into adipocytes (adiposomes indicated by arrows of FIGS. 2-a) (FIG. 2-a: lower row).

Mouse MSCs coexpressing PDGFRα and Sca-1 on their cell surfaces are known to be high-quality MSCs maintaining an undifferentiated state (Non-patent Literatures 4 and 5). OriCell™ mouse MSCs passaged 7 times by adherent culture retained about 90% of PDGFRα/Sca-1$^+$ (copositive fraction) (not shown), but when the passaging was repeated thereafter, the copositive fraction was reduced to 46.1% at 8 passages (FIG. 2-b: left figure) and reduced to 25.0% at 23 passages (not shown).

However, when even OriCell™ mouse MSCs repeatedly passaged many times (44 times) by adherent culture were subjected to shaking culture for 2 months to form cell constructs, the copositive fraction of cells that had migrated and grown from the cell constructs was restored to 68.3% (FIG. 2-b: right figure).

The results of RT-PCR analysis revealed that the OriCell™ mouse MSCs cultured by adherent culture highly expressed the PDGFRα gene at a passage number of 9, but as the passage number increased to 25 and to 41, the expression of the PDGFRα gene was markedly reduced, suggesting the possibility that undifferentiated potency had been lost.

However, when even OriCell™ mouse MSCs repeatedly passaged 37 times were subjected to shaking culture for 2 months to form cell constructs, it was confirmed that a state in which the PDGFRα gene was highly expressed was restored (FIG. 2-C).

FIG. 3: Mesodermal Differentiation of Oricell™ Mouse MSCs Subjected to Shaking Culture The Oricell™ mouse MSCs were used to prepare cells having a small passage number in adherent culture (passage number: 9) and cells having a large passage number in adherent culture (passage number: 30 times), which were subjected to shaking culture for 1 month and then induced to differentiate into mesodermal cells, specifically osteoblasts, chondrocytes, and adipocytes. The results are shown in FIG. 3.

Both the cells having a small passage number in adherent culture (passage number: 9) and cells having a large passage number in adherent culture (passage number: 30) that had been induced to differentiate after shaking culture showed abilities to differentiate into osteoblasts (ALP-positive), chondrocytes (toluidine blue-positive), and adipocytes (Oil Red O-positive).

FIG. 4: Tissue-Specific Gene Expression Analysis (RT-PCR) at Time of Induction of Differentiation into Mesodermal Cells The Oricell™ mouse MSCs were used to prepare cells having a small adherent passage number (passage number: 8 or 9) and cells having a large adherent passage number (passage number: 30). Cells subjected to differentiation induction immediately after adherent culture and cells subjected to shaking culture after adherent culture before differentiation induction were each analyzed for the expressions of genes associated with osteoblasts, chondrocytes, and adipocytes through the use of RT-PCR.

When differentiation into osteoblasts was induced for 21 days, in the case of the cells having a small passage number in adherent culture (passage number: 8 or 9), the shaking-cultured cells had higher expressions of osteoblast markers OCN and OPN as compared to the adherent-cultured cells. In the case of the cells having a large adherent passage number (passage number: 30), the shaking-cultured cells had a higher expression of OPN as compared to the adherent-cultured cells (FIG. 4-a).

Differentiation into chondrocytes was induced for 21 days, in the case of the cells having a small passage number in adherent culture (passage number: 8 or 9), the shaking-cultured cells had higher expressions of chondrocyte markers Agrican, Sox9, and Col2A1 as compared to the adherent-cultured cells. In the case of the cells having a large adherent passage number (passage number: 30), the shaking-cultured cells had higher expressions of Agrican and Sox9 as compared to the adherent-cultured cells (FIG. 4-b).

When differentiation into adipocytes was induced for 21 days, the cells subjected to adherent culture did not express adipocyte markers Adipsin and PPARγ irrespective of the passage number. Meanwhile, when the cells having a small adherent passage number (passage number: 9) were subjected to shaking culture, marked expressions of Adipsin and PPARγ were found, and when the cells having a large adherent passage number (passage number: 30) were subjected to shaking culture, the expression of PPARγ was found (FIG. 4-c).

Figure 5A:
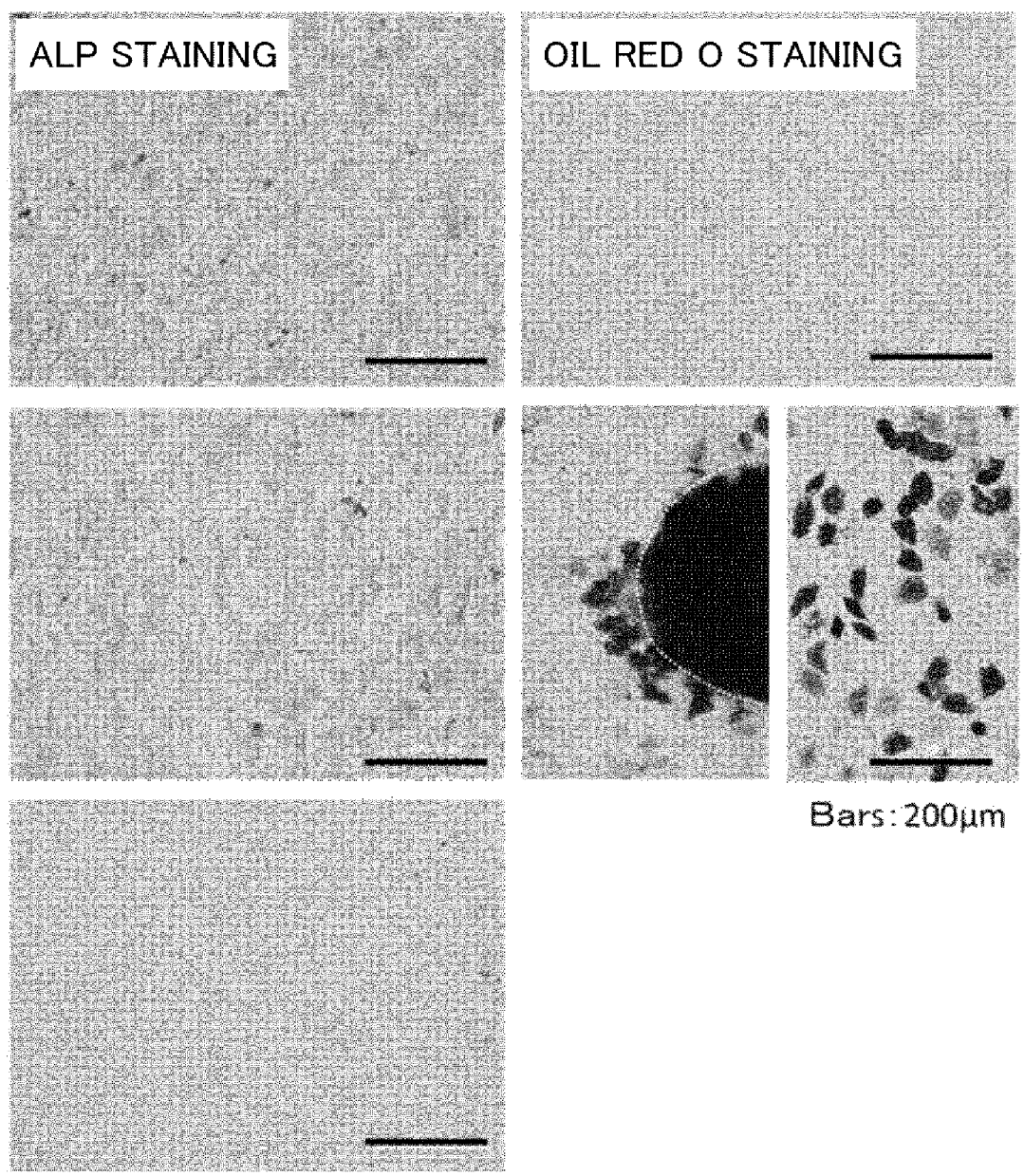
FIG. 5 are photographs and graphs for showing the influence of shaking culture on the maintenance of the differentiation ability of human MSCs. Left column of FIG. 5a: osteoblasts. Right column of FIG. 5a: adipocytes. Upper row of FIG. 5a: 20 adherent passages. Middle row of FIG. 5a: shaking culture after 6 adherent passages. Lower row of FIG. 5a: 20 adherent passages without bone differentiation induction. Upper row of FIG. 5b: 21 adherent passages. Lower row of FIG. 5b: shaking culture after 7 adherent passages.
FIG. 5c: Numbers above FIG. 5c each represent an adherent passage number (number of passages).
Figure 5C:
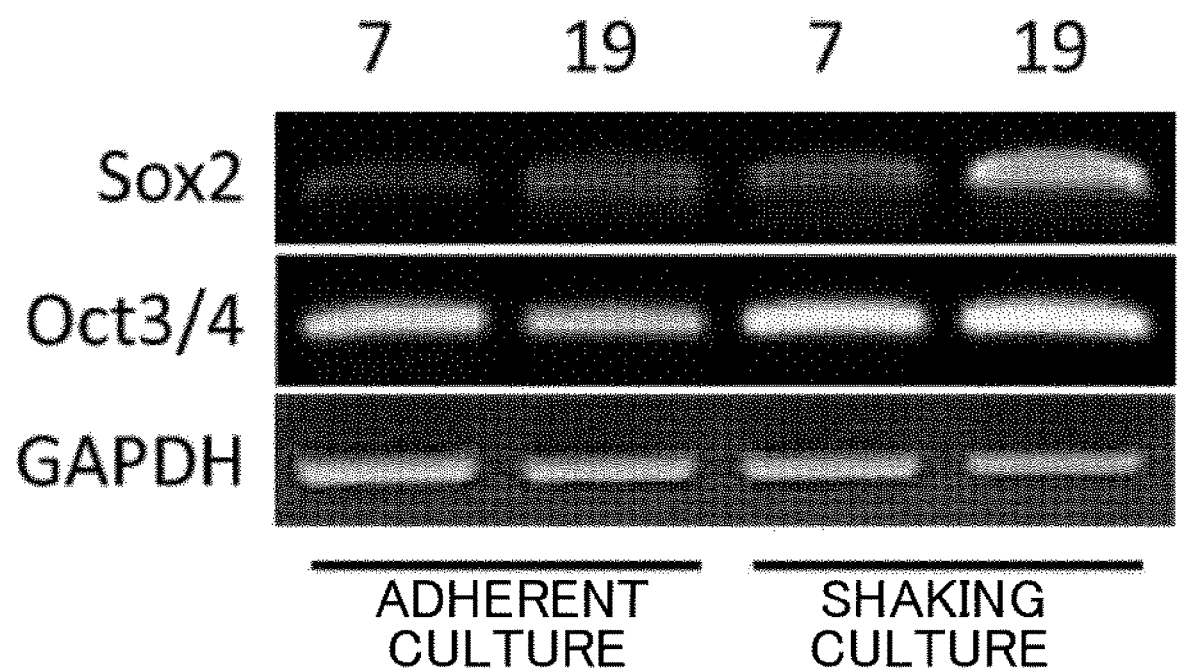

FIG. 5: Influence of Shaking Culture on Maintenance of Differentiation Ability of Human MSCs The influence of shaking culture on the maintenance of the differentiation ability of human MSCs was investigated. In adherent culture, when the human MSCs were repeatedly passaged 20 times, the cells showed an ability to differentiate into osteoblasts (ALP staining-positive), but had lost an ability to differentiate into adipocytes (Oil Red O staining-negative) (FIG. 5-a: upper row).

However, when human MSCs passaged 6 times by adherent culture were subjected to shaking culture for 2 months to form cell constructs, cells that had migrated and grown from the cell constructs retained not only an ability to differentiate into osteoblasts (ALP staining-positive) but also a high ability to differentiate into adipocytes (Oil Red O staining-positive) (FIG. 5-a: middle row). In particular, cells that had migrated to the peripheries of the cell constructs adhering to the culture dish formed many adiposomes, indicating the possibility of high undifferentiation. When human MSCs passaged 6 times were subjected to adherent culture for 2 months in the same manner as in the shaking culture, the cells reached a passage number of 12 and had already lost an ability to differentiate into fat (Oil Red O staining-negative: not shown).

Human MSCs expressing CD271 (LNGFR), CD90 (Thy-1), and CD106 (VCAM-1) on their cell surfaces are known to be high-quality MSCs maintaining an undifferentiated state (Non-patent Literature 7). Human MSCs passaged 21 times by adherent culture highly expressed CD90 (FIG. 5-b: upper left figure). Similarly, cells that had migrated and grown from cell constructs formed by subjecting human MSCs passaged 7 times by adherent culture to shaking culture for 2 months also maintained the expression of CD90 at a high level of from 97.9% to 98.0% (FIG. 5-b: lower left figure). Meanwhile, the expression of CD271 in the human MSCs passaged 7 times by adherent culture had already been reduced, and its expression was not restored even by shaking culture (not shown).

However, the results of FACS analysis for CD106 serving as a cell surface marker for high-quality MSCs (Non-patent Literature 7) revealed that its expression had been reduced to from 6.0% to 7.5% in the human MSC cells passaged 21 times by adherent culture (FIG. 5-b: upper right figure), but its expression had been maintained at from 59.6% to 87.1% in the cells that had migrated and grown from the cell constructs formed by subjecting the human MSCs passaged 7 times by adherent culture to shaking culture for 2 months (FIG. 5-b: lower right figure).

The results of RT-PCR analysis revealed that the human MSCs cultured by adherent culture expressed the Oct3/4 gene known to be an undifferentiated stem cell marker at a passage number of 7, but when the passage number increased to 19, its expression was reduced, suggesting the possibility that undifferentiated potency had been lost. However, when even human MSCs repeatedly passaged 19 times were subjected to shaking culture for 2 months to form cell constructs, it was confirmed that a state in which the Sox2 and Oct3/4 genes known to be stem cell-associated markers were highly expressed was restored (FIG. 5-C).

FIG. 6: Cartilage Differentiation Ability of Human MSCs

The human MSCs were used to prepare cells having a small adherent passage number (passage number: 9) and cells having a large adherent passage number (passage number: 19), which were analyzed for an ability to differentiate into chondrocytes.

When the cells having a small adherent passage number (passage number: 9) that had been subjected to differentiation induction immediately after adherent culture were induced to differentiate into cartilage for 21 days, the formation of pellets was found but there were few cells positive for toluidine blue for staining cartilage matrix. Meanwhile, when the cells having a small adherent passage number (passage number: 9) were induced to differentiate into cartilage after being subjected to shaking culture, the formation of pellets by toluidine blue-positive cells was found (FIG. 6-a).

When the cells having a large adherent passage number (passage number: 19) that had been subjected to differentiation induction immediately after adherent culture were induced to differentiate into cartilage for 21 days, the formation of pellets was not found. Meanwhile, when the cells having a large adherent passage number (passage number: 19) were induced to differentiate into cartilage after being subjected to shaking culture, the formation of pellets by toluidine blue-positive cells was found (FIG. 6-b).

Figure 7A:
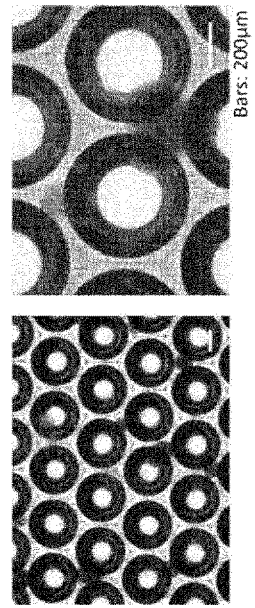
FIG. 7a: human MSCs (used after 9 adherent passages). 7 days of culture.
Figure 7B:
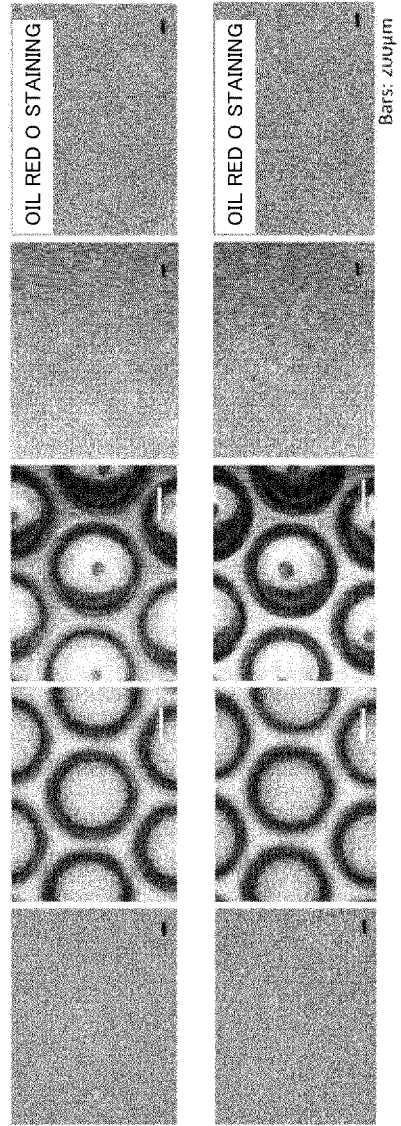
FIG. 7b: mouse MSCs. Upper row of FIG. 7b: used after 25 adherent passages (Second from left: three-dimensional suspension culture vessel, immediately after seeding. Third from left: three-dimensional suspension culture vessel, day 7 of culture. Fourth from left: readhesion to culture dish, day 7 from readhesion. Fifth from left: readhesion to culture dish, fat differentiation induction). Lower row of FIG. 7b: used after 41 adherent passages (Second from left: three-dimensional suspension culture vessel, immediately after seeding. Third from left: three-dimensional suspension culture vessel, day 7 of culture. Fourth from left: readhesion to culture dish, day 7 from readhesion. Fifth from left: readhesion to culture dish, fat differentiation induction).

FIG. 7: Adherent Culture of MSC Cell Constructs Using Three-Dimensional Suspension Culture Vessel (Related Art)

Human MSCs (passage number: 9) or OriCell™ mouse MSCs (passage numbers: 25 and 41) subjected to maintenance culture by adherent culture were seeded at $3\times10^6$ cells/ml in a low-attachment three-dimensional culture vessel (Kuraray Elplasia RB 500 400 NA Plate) used for an existing method of forming cell constructs of MSCs. As a result, the human MSCs adhered to the culture dish, and did not achieve the formation of cell constructs even after 7 days (FIG. 7-a). Meanwhile, the mouse MSCs formed cell constructs after 7 days of culture in the culture vessel as reported by Baraniak et al. (Non-patent Literature 10) (FIG. 7-b). The cell constructs collected at this point of time were transferred again to a culture dish and left to stand still under an adherent culture environment. As a result, the cell constructs adhered to the culture dish and the cells migrated to the periphery thereof, but the morphology of the cell constructs disappeared after 7 days instead of being kept, i.e., the ability thereof to differentiate into adipocytes had been lost (Oil Red O staining-negative with no adiposomes found) (FIGS. 7-b).

Figure 8A:
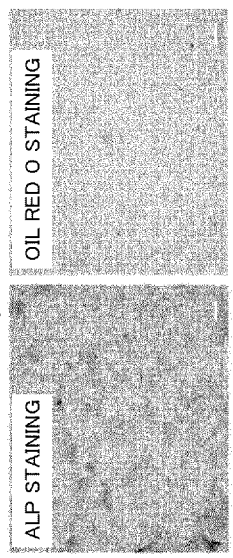
FIG. 8a: used after 25 adherent passages (Left of FIG. 8a: bone. Right of FIG. 8a: fat).
Figure 8B:
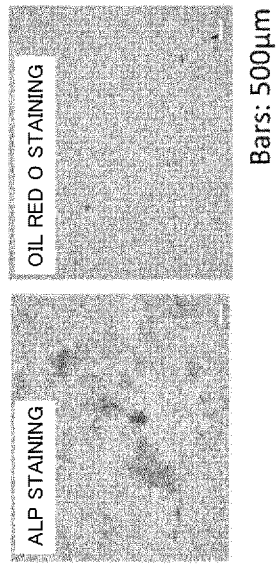
FIG. 8b: used after 41 adherent passages (Left of FIG. 8b: osteoblasts. Right of FIG. 8b: adipocytes)

FIG. 8: Differentiation Ability Analysis of OriCell™ Mouse MSC Cell Constructs Using Three-Dimensional Suspension Culture Vessel (Related Art)

Oricell™ mouse MSCs (passage numbers: 25 and 41) subjected to maintenance culture by adherent culture were seeded at $3\times10^6$ cells/ml in a low-attachment three-dimensional suspension culture vessel (Kuraray Elplasia RB 500 400 NA Plate). After 7 days, formed cell constructs were seeded in a 12-well plate (Cat. #665-180: CELLSTAR, greiner bio-one) to make a transition to adherent culture, and the differentiation of cells that had migrated from the adhered cell constructs into osteoblasts and adipocytes was investigated.

Oricell™ mouse MSCs after 25 adherent passages and after 41 adherent passages were induced to differentiate into osteoblasts for 21 days, and as a result, both the cells were ALP-positive, confirming an ability to differentiate into osteoblasts (FIG. 8-a). Meanwhile, Oricell™ mouse MSCs after 25 adherent passages and after 41 adherent passages were induced to differentiate into adipocytes for 21 days, and as a result, the formation of Oil Red O-positive adiposomes was not found (FIGS. 8-b).

FIG. 9: Morphology Retention and Cell Supply Ability of Human MSC Cell Construct Subjected to Shaking Culture Cell constructs formed by subjecting human MSCs passaged 7 times by adherent culture to shaking culture for 2 months were left to stand still in a culture dish, and as a result, the migration of cells to the peripheries of the cell constructs was found next day and the cells grew to fill the culture dish after 7 days (FIG. 9-a: upper row). In addition, the readhered cell constructs retained their morphology even after 7 days, and the cell constructs were able to be mechanically detached and left to stand still in a fresh culture dish (first time of readhesion). The day after the cell constructs were again left to stand still, as in the foregoing, the migration of cells to the peripheries of the cell constructs was found, the cells grew to fill the culture dish within 10 days, and the cell constructs retained their morphology (FIG. 9-a: two left photographs in middle row). Even when the cell constructs were further mechanically detached and left to stand still in a fresh culture dish repeatedly 4 times (second to fifth times of readhesion), similarly, the migration of cells to the peripheries of the cell constructs was found, the cells grew to fill the culture dish within 14 days, and the cell constructs retained their morphology (FIG. 9-a: three right photographs in middle row, and lower row).

In addition, when the step of detaching the cell constructs and allowing the cell constructs to adhere to a culture dish again was performed 3 times, the migratory cells showed an ability to differentiate into osteoblasts (ALP staining-positive) and an ability to differentiate into adipocytes (adiposomes and Oil Red O staining-positive), thus revealing that undifferentiation was maintained (FIGS. 9-b). Thus, it has been found that the MSC cell construct according to the present invention has robust adhesion between cells, and even when the cell construct is returned again to an adherent culture environment, the cell construct continuously supplies undifferentiated MSCs to the culture dish without losing its morphology.

Figure 10B:
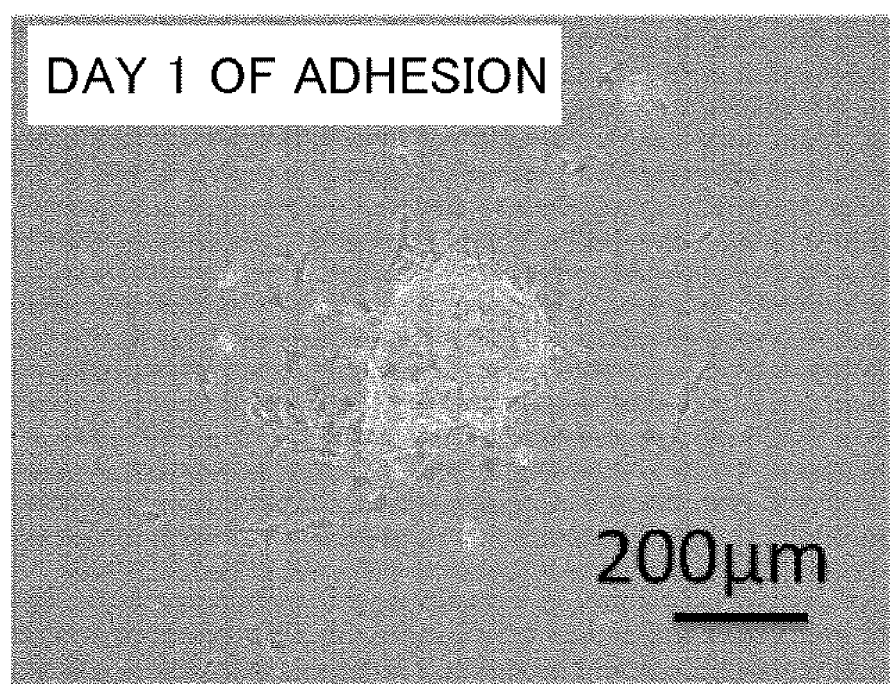
FIG. 10b and FIG. 10c: Shaking culture was performed after 2 adherent passages, and after a cell construct had been formed, the cell construct was allowed to readhere to a culture dish.
Figure 10C:
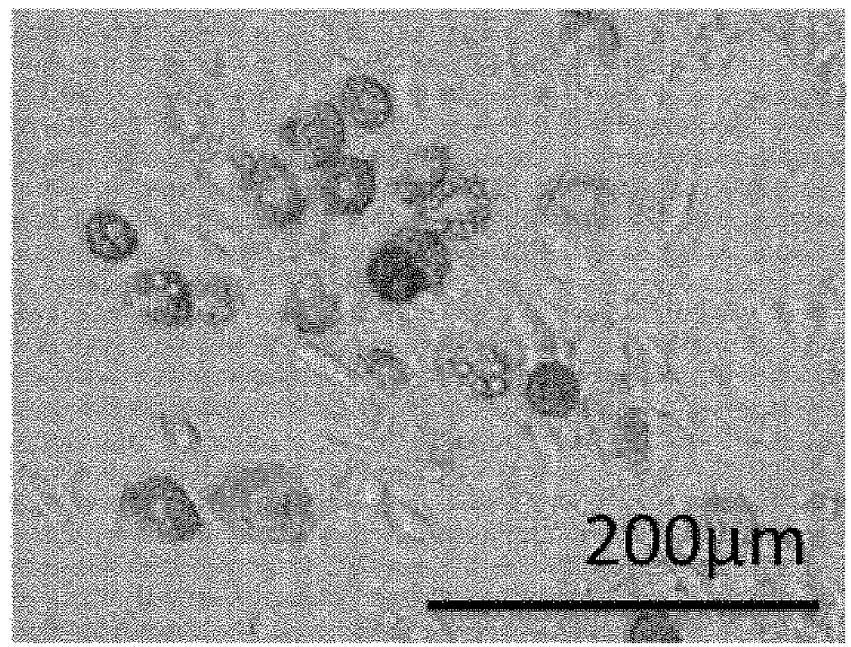

FIG. 10: Cell Construct Formed by Shaking Culture of Purified Mouse MSCs

An investigation was made as to whether or not purified mouse MSCs also formed cell constructs like those in the case of OriCell™ mouse MSCs through shaking culture. Purified mouse MSCs after sorting were passaged twice by adherent culture in order to secure a number of cells. The purified mouse MSCs passaged twice ($5.0\times10^5$ cells/flask) were subjected to shaking culture for 2 months, and as a result, formed cell constructs like those in the case of the OriCell™ mouse MSCs (not shown). The formed cell constructs were left to stand still in a fresh culture dish, and as a result, the migration of cells to the peripheries of the cell constructs was found next day (FIG. 10-b: left figure), and the migratory cells grew to fill the culture dish within 10 days. Also in this case, the cell constructs retained their morphology without losing shape. In addition, When the cells that had migrated and grown were induced to differentiate into adipocytes, adiposomes were produced after 14 days (FIG. 10-c), revealing that an ability thereof to differentiate into adipocytes was retained.

FIG. 11: Formation of Cell Construct of OriCell™ Mouse MSCs Using Neural Stem Cell Medium An investigation was made as to whether or not a cell construct was formed also in the case where the OriCell™ mouse MSCs were used and subjected to similar shaking culture in the neural stem cell medium. In addition, an obtained cell construct was investigated for an ability to differentiate into mesodermal cells (bone, fat, and cartilage) and neuronal cells. Further, the expressions of neural crest stem cell markers Nestin and Twist and the expression of a mesenchymal stem cell marker PDGFRα were analyzed by RT-PCR.

Cells subjected to few adherent passages (passage number: 9) were subjected to shaking culture in the neural stem cell medium, and as a result, the formation of a cell construct was found within 1 month (FIG. 11-a).

This cell construct was used and induced to differentiate into osteoblasts, chondrocytes, and adipocytes, and as a result, ALP-positive osteoblasts, adipocytes showing Oil Red O-positive adiposomes, and the formation of cartilage pellets by toluidine blue-positive cells were found (FIG. 11-*b*). In addition, this cell construct was used and induced to differentiate into neuronal cells, and as a result, βIII-Tublin-positive neuronal cells were found (FIG. 11-*c*).

Further, even cells subjected to many adherent passages (passage number: 39) were able to form a cell construct through the use of the neural stem cell medium (FIG. 11-*d*). The results of RT-PCR analysis revealed that the cells of this cell construct markedly expressed the neural crest stem cell markers Nestin and Twist and the mesenchymal stem cell marker PDGFRα (FIG. 11-*e*).

CONCLUSION

As apparent from the above-mentioned results, through the use of the shaking culture, MSCs that had lost undifferentiation were able to be restored again to a cell construct of an MSC population of high undifferentiation. In addition, the MSC cell construct formed by the shaking culture retains undifferentiation, and at the same time, has a robust morphology retention ability, and hence can supply undifferentiated MSCs when allowed to readhere to a fresh culture dish.

INDUSTRIAL APPLICABILITY

According to the method of the present invention, through the culture of MSCs by quite a novel agitation shaking culture method from an adherent environment, a robust three-dimensional MSC construct (sphere) maintaining a differentiation ability and maintaining a morphology can be formed.

Therefore, it is suggested that the MSC construct is useful as a stem cell pool for continuously supplying stem cells retaining undifferentiation.

In addition, from the viewpoint of application to regenerative medicine, this cell construct itself can be expected to serve as a scaffold for space making at a defective site, to thereby promote tissue regeneration with stem cells.

The invention claimed is:

1. A method of keeping mesenchymal stem cells undifferentiated, the method comprising culturing mesenchymal stem cells by shaking suspension culture to obtain cell constructs.

2. The method according to claim 1, wherein the culturing is performed by shaking suspension culture at a rotational speed of from 20 rpm to 200 rpm.

3. The method according to claim 1, wherein the culturing is performed by shaking suspension culture at an amplitude of from 10 mm to 40 mm.

4. The method according to claim 1, further comprising passaging the mesenchymal stem cells 2 or more times.

5. The method according to claim 1, wherein the mesenchymal stem cells to be subjected to the shaking suspension culture are cells that have been passaged to the point where the cells have lost an ability to differentiate into predetermined cells, and the ability to differentiate into predetermined cells is restored by the shaking suspension culture.

6. The method according to claim 5, wherein the shaking suspension culture occurs for 10 days or more.

7. The method according to claim 1, wherein the shaking suspension culture occurs for 10 days or more.

* * * * *

```
                              SEQUENCE LISTING

<160> NUMBER OF SEQ ID NOS: 28

<210> SEQ ID NO 1
<211> LENGTH: 20
<212> TYPE: DNA
<213> ORGANISM: Artificial Sequence
<220> FEATURE:
<223> OTHER INFORMATION: primer

<400> SEQUENCE: 1
tacatcatcc ccctgccaga                                                      20

<210> SEQ ID NO 2
<211> LENGTH: 20
<212> TYPE: DNA
<213> ORGANISM: Artificial Sequence
<220> FEATURE:
<223> OTHER INFORMATION: primer

<400> SEQUENCE: 2
aaggttatcc cgaggaggct                                                      20

<210> SEQ ID NO 3
<211> LENGTH: 20
<212> TYPE: DNA
<213> ORGANISM: Artificial Sequence
<220> FEATURE:
<223> OTHER INFORMATION: primer

<400> SEQUENCE: 3
caccatggag aaggccgggg                                                      20

<210> SEQ ID NO 4
<211> LENGTH: 20
<212> TYPE: DNA
<213> ORGANISM: Artificial Sequence
<220> FEATURE:
<223> OTHER INFORMATION: primer

<400> SEQUENCE: 4
gacggacaca ttgggggtag                                                      20

<210> SEQ ID NO 5
<211> LENGTH: 26
```

```
<212> TYPE: DNA
<213> ORGANISM: Artificial Sequence
<220> FEATURE:
<223> OTHER INFORMATION: primer

<400> SEQUENCE: 5
gggaaatggg aggggtgcaa aagagg                                    26

<210> SEQ ID NO 6
<211> LENGTH: 26
<212> TYPE: DNA
<213> ORGANISM: Artificial Sequence
<220> FEATURE:
<223> OTHER INFORMATION: primer

<400> SEQUENCE: 6
ttgcgtgagt gtggatggga ttggtg                                    26

<210> SEQ ID NO 7
<211> LENGTH: 24
<212> TYPE: DNA
<213> ORGANISM: Artificial Sequence
<220> FEATURE:
<223> OTHER INFORMATION: primer

<400> SEQUENCE: 7
gacaggggga ggggaggagc tagg                                      24

<210> SEQ ID NO 8
<211> LENGTH: 26
<212> TYPE: DNA
<213> ORGANISM: Artificial Sequence
<220> FEATURE:
<223> OTHER INFORMATION: primer

<400> SEQUENCE: 8
cttccctcca accagttgcc ccaaac                                    26

<210> SEQ ID NO 9
<211> LENGTH: 20
<212> TYPE: DNA
<213> ORGANISM: Artificial Sequence
<220> FEATURE:
<223> OTHER INFORMATION: primer

<400> SEQUENCE: 9
gtcaaggccg agaatgggaa                                           20

<210> SEQ ID NO 10
<211> LENGTH: 20
<212> TYPE: DNA
<213> ORGANISM: Artificial Sequence
<220> FEATURE:
<223> OTHER INFORMATION: primer

<400> SEQUENCE: 10
gcttcaccac cttcttgatg                                           20

<210> SEQ ID NO 11
<211> LENGTH: 20
<212> TYPE: DNA
<213> ORGANISM: Artificial Sequence
<220> FEATURE:
<223> OTHER INFORMATION: primer

<400> SEQUENCE: 11
```
tcaccattcg gatgagtctg                                              20

<210> SEQ ID NO 12
<211> LENGTH: 20
<212> TYPE: DNA
<213> ORGANISM: Artificial Sequence
<220> FEATURE:
<223> OTHER INFORMATION: primer

<400> SEQUENCE: 12
acttgtggct ctgatgttcc                                              20

<210> SEQ ID NO 13
<211> LENGTH: 18
<212> TYPE: DNA
<213> ORGANISM: Artificial Sequence
<220> FEATURE:
<223> OTHER INFORMATION: primer

<400> SEQUENCE: 13
aagcaggagg gcaataag                                                18

<210> SEQ ID NO 14
<211> LENGTH: 20
<212> TYPE: DNA
<213> ORGANISM: Artificial Sequence
<220> FEATURE:
<223> OTHER INFORMATION: primer

<400> SEQUENCE: 14
agctgctgtg acatccatac                                              20

<210> SEQ ID NO 15
<211> LENGTH: 22
<212> TYPE: DNA
<213> ORGANISM: Artificial Sequence
<220> FEATURE:
<223> OTHER INFORMATION: primer

<400> SEQUENCE: 15
actccctgtc cgcccctgaa cc                                           22

<210> SEQ ID NO 16
<211> LENGTH: 24
<212> TYPE: DNA
<213> ORGANISM: Artificial Sequence
<220> FEATURE:
<223> OTHER INFORMATION: primer

<400> SEQUENCE: 16
cgagagcccc acgtaaccac acct                                         24

<210> SEQ ID NO 17
<211> LENGTH: 22
<212> TYPE: DNA
<213> ORGANISM: Artificial Sequence
<220> FEATURE:
<223> OTHER INFORMATION: primer

<400> SEQUENCE: 17
gtgcgatcaa agtagaacct gc                                           22

<210> SEQ ID NO 18
<211> LENGTH: 24
<212> TYPE: DNA
<213> ORGANISM: Artificial Sequence

```
<220> FEATURE:
<223> OTHER INFORMATION: primer

<400> SEQUENCE: 18
cctatcataa ataagcttca atcg                                           24

<210> SEQ ID NO 19
<211> LENGTH: 20
<212> TYPE: DNA
<213> ORGANISM: Artificial Sequence
<220> FEATURE:
<223> OTHER INFORMATION: primer

<400> SEQUENCE: 19
cgccactttc atgaccgaga                                                20

<210> SEQ ID NO 20
<211> LENGTH: 24
<212> TYPE: DNA
<213> ORGANISM: Artificial Sequence
<220> FEATURE:
<223> OTHER INFORMATION: primer

<400> SEQUENCE: 20
tcattcagac cgatccactg gtag                                           24

<210> SEQ ID NO 21
<211> LENGTH: 23
<212> TYPE: DNA
<213> ORGANISM: Artificial Sequence
<220> FEATURE:
<223> OTHER INFORMATION: primer

<400> SEQUENCE: 21
ccttcaacct tcctcactac agc                                            23

<210> SEQ ID NO 22
<211> LENGTH: 20
<212> TYPE: DNA
<213> ORGANISM: Artificial Sequence
<220> FEATURE:
<223> OTHER INFORMATION: primer

<400> SEQUENCE: 22
ggtggagtag agccctgagc                                                20

<210> SEQ ID NO 23
<211> LENGTH: 21
<212> TYPE: DNA
<213> ORGANISM: Artificial Sequence
<220> FEATURE:
<223> OTHER INFORMATION: primer

<400> SEQUENCE: 23
cctccgtcta ctgtccactg a                                              21

<210> SEQ ID NO 24
<211> LENGTH: 20
<212> TYPE: DNA
<213> ORGANISM: Artificial Sequence
<220> FEATURE:
<223> OTHER INFORMATION: primer

<400> SEQUENCE: 24
attggagccc tggatgagca                                                20
```

```
<210> SEQ ID NO 25
<211> LENGTH: 22
<212> TYPE: DNA
<213> ORGANISM: Artificial Sequence
<220> FEATURE:
<223> OTHER INFORMATION: primer

<400> SEQUENCE: 25
aatgggagga tggagaatgg ac                                            22

<210> SEQ ID NO 26
<211> LENGTH: 21
<212> TYPE: DNA
<213> ORGANISM: Artificial Sequence
<220> FEATURE:
<223> OTHER INFORMATION: primer

<400> SEQUENCE: 26
tagacaggca gggctagcaa g                                             21

<210> SEQ ID NO 27
<211> LENGTH: 20
<212> TYPE: DNA
<213> ORGANISM: Artificial Sequence
<220> FEATURE:
<223> OTHER INFORMATION: primer

<400> SEQUENCE: 27
ggaggatgga gggggcctgg                                               20

<210> SEQ ID NO 28
<211> LENGTH: 19
<212> TYPE: DNA
<213> ORGANISM: Artificial Sequence
<220> FEATURE:
<223> OTHER INFORMATION: primer

<400> SEQUENCE: 28
tgtgccccac gccctgatt                                                19
```